United States Patent
Masuko et al.

(10) Patent No.: US 9,725,519 B2
(45) Date of Patent: Aug. 8, 2017

(54) ANTIBODY AGAINST TRANSPORTER AND USE THEREOF

(71) Applicants: Kinki University, Higashiosaka-shi, Osaka (JP); Link Genomics, Inc., Chuo-ku, Tokyo (JP)

(72) Inventors: Takashi Masuko, Osaka (JP); Shinichiro Niwa, Tokyo (JP); Hidemi Hayashi, Tokyo (JP); Dai Ogura, Tokyo (JP); Takayuki Shindou, Tokyo (JP)

(73) Assignees: Kinki University, Osaka (JP); Link Genomics, Inc., Tokyo (JP)

( * ) Notice: Subject to any disclaimer, the term of this patent is extended or adjusted under 35 U.S.C. 154(b) by 0 days.

(21) Appl. No.: 14/561,944

(22) Filed: Dec. 5, 2014

(65) Prior Publication Data

US 2015/0147278 A1 May 28, 2015

Related U.S. Application Data

(63) Continuation-in-part of application No. PCT/JP2013/065996, filed on Jun. 10, 2013.

(30) Foreign Application Priority Data

Jun. 8, 2012 (JP) .................. 2012-131424

(51) Int. Cl.
| | | |
|---|---|---|
| C07K 16/30 | (2006.01) | |
| G01N 33/574 | (2006.01) | |
| A61K 39/395 | (2006.01) | |
| C07K 16/28 | (2006.01) | |
| A61K 35/17 | (2015.01) | |
| A61K 47/48 | (2006.01) | |
| A61K 51/10 | (2006.01) | |

(52) U.S. Cl.
CPC ............. *C07K 16/30* (2013.01); *A61K 35/17* (2013.01); *A61K 47/48569* (2013.01); *A61K 51/1045* (2013.01); *C07K 16/2896* (2013.01); *C07K 16/303* (2013.01); *C07K 16/3015* (2013.01); *C07K 16/3023* (2013.01); *C07K 16/3038* (2013.01); *C07K 16/3046* (2013.01); *C07K 16/3053* (2013.01); *C07K 16/3061* (2013.01); *C07K 16/3069* (2013.01); *G01N 33/57492* (2013.01); *C07K 2317/21* (2013.01); *C07K 2317/24* (2013.01); *C07K 2317/32* (2013.01); *C07K 2317/54* (2013.01); *C07K 2317/55* (2013.01); *C07K 2317/56* (2013.01); *C07K 2317/565* (2013.01); *C07K 2317/622* (2013.01); *C07K 2317/624* (2013.01); *C07K 2317/626* (2013.01); *C07K 2317/73* (2013.01); *C07K 2317/732* (2013.01); *C07K 2317/77* (2013.01); *G01N 2333/70596* (2013.01)

(58) Field of Classification Search
CPC .... C07K 16/30; C07K 16/2896; A61K 35/17; A61K 47/48569; A61K 51/1045; G01N 33/57492
See application file for complete search history.

(56) References Cited

U.S. PATENT DOCUMENTS

| | | | |
|---|---|---|---|
| 2010/0143367 A1 | 6/2010 | Tahara et al. | |
| 2013/0302353 A1* | 11/2013 | Medema ............ | C07K 16/2875 424/173.1 |

FOREIGN PATENT DOCUMENTS

| | | |
|---|---|---|
| JP | 2011-024537 A | 2/2011 |
| WO | WO 2007/114496 A1 | 10/2007 |
| WO | WO 2010/100056 A2 | 9/2010 |
| WO | WO 2011/017294 A1 | 2/2011 |

OTHER PUBLICATIONS

Almagro & Fransson, Frontiers in Bioscience 2008; 13:1619-33.*
Rudikoff et al., Proc. Nat'l Acad. Sci. USA 1982; 79:1979-83.*
Brown et al., J. Immunol. 1996; 156(9):3285-91.*
Reichert & Valge-Archer, Nat. Rev. Drug Disc. 2007; 6:349-356.*
Gross & Eshhar, Annu. Rev. Pharmacol. Toxicol. 2016; 56:59-83.*
Tse et al., Clin Cancer Res, 2006; 12(4):1373-82.*
HogenEsch et al. J. Controlled Release 2012; 164:183-186.*
Tang et al. Cancer Letters 2016; 370:85-90.*
Balmana et al. Ann Oncol 2009; 20(supp 4):iv19-20.*
Bartolazzi et al., The Lancet 2008; 9:543-49.*
Nakamura et al. "4F2 (CD98) Heavy Chain is Associated Covalently with an Amino Acid Transporter and Controls Intracellular Trafficking and Membrane Topology of 4F2 Heterodimer," The Journal of Biological Chemistry, Jan. 29, 1999, 274(6):3009-3015.
Haynes et al., "Characterization of a monoclonal antibody (4F2) that binds to human monocytes and to a subset of activated lymphocytes," The Journal of Immunology, Apr. 1981, 126(4):1409-1414.
Kaira et al., "L-type amino acid transporter 1 and CD98 expression in primary and metastatic sites of human neoplasms," Cancer Sci., Dec. 2008, 99(12):2380-2386.
Kaira et al., "Prognostic significance of L-type amino acid transporter 1 (LAT1) and 4F2 heavy chain (CD98) expression in early stage squamous cell carcinoma of the lung," Cancer Sci., Feb. 2009, 100(2):249-254.
Kanai et al., "Broad scope amino acid transporters: LAT family," Protein, Nucleic Acid and Enzyme (Tanpakushitsu, Kakusan, Koso), 2001, 46(5):629-637.

(Continued)

*Primary Examiner* — Jessica H Roark
(74) *Attorney, Agent, or Firm* — Foley & Lardner LLP

(57) ABSTRACT

The present invention provides a prophylactic or therapeutic agent for various malignant tumors, including currently intractable solid tumors, which contains an antibody having the ability to bind to human LAT1/CD98 and inducing antibody-dependent cellular cytotoxicity specifically against cancer cells as an active ingredient.

31 Claims, 3 Drawing Sheets

(56) References Cited

OTHER PUBLICATIONS

Masuko et al., "Human bladder cancer cell-surface antigens recognized by murine monoclonal antibodies raised against T24 bladder cancer cells," Jpn. J. Cancer Res. (Gann), May 1985, 76:386-394.
Ohkawa et al., "Oncogenicity of L-type amino-acid transporter 1 (LAT1) revealed by targeted gene disruption in chicken DT40 cells: LAT1 is a promising molecular target for human cancer therapy," Biochemical and Biophysical Research Communications, 2011, 405:649-655.
Ohno et al., "Production and characterization of highly tumor-specific rat monoclonal antibodies recognizing the extracellular domain of human L-type amino-acid transporter 1," Cancer Sci., May 2008, 99(5):1000-1007.
Yanagida et al., "Human L-type amino acid transporter 1 (LAT1): characterization of function and expression in tumor cell lines," Biochimica et Biophysica Acta, 2001, 1514:291-302.

\* cited by examiner

ANTIBODY AGAINST TRANSPORTER AND USE THEREOF

CROSS-REFERENCE TO RELATED APPLICATIONS

This application is a Continuation-In-Part of PCT/JP2013/065996, filed Jun. 10, 2013, which claims priority from Japanese application JP 2012-131424, filed Jun. 8, 2012, the entire contents of which are incorporated herein by reference.

SEQUENCE LISTING

The instant application contains a Sequence Listing which has been submitted in ASCII format via EFS-WEB and is hereby incorporated by reference in its entirety. Said ASCII copy, created on Dec. 30, 2014, is named 023312-0228 SL.txt and is 21 KB.

TECHNICAL FIELD

The present invention relates to an anti-LAT1/CD98 monoclonal antibody, which specifically binds to the extracellular region of the LAT1/CD98 complex to directly inhibit amino acid transport activity or indirectly induce cytotoxic factors in cooperation with lymphocytes, thereby leading tumor cells to cell death. The present invention further relates to an antibody and/or immunoconjugate composition, as well as the use thereof for treatment, prevention and/or diagnosis of tumor.

BACKGROUND ART

Organisms have various mechanisms in order to obtain, e.g., nutrients and signal transmitters required for their vital activities, and many different transporters and receptors present on their respective cell membranes are a few examples of these mechanisms. Among them, the transport of amino acids, which are major elements constituting the living body, has been studied since the 1960s. Molecules responsible for amino acid transport have been identified starting in 1990, and approximately 30 types of dominant genes have now been identified. These transporters are broadly divided into three types, i.e., basic amino acid transporters, neutral amino acid transporters and acidic amino acid transporters, depending on the nature of amino acids to be transported. However, there are six members, including LAT1 described below, for amino acid transporters heterodimerized with CD98.

LAT1 is a sodium-independent neutral amino acid transporter which has relatively broader substrate selectivity than other transporters. LAT1 is a twelve-transmembrane protein cloned in 1998 and is present on the cell membrane surface. LAT1 is one of the six members of CD981c and forms a heterodimer when disulfide bonded with a single transmembrane protein, 4F2hc(CD98), thereby exerting amino acid transport activity. 4F2hc is a chaperone-like molecule which binds to a specific transporter for migration to the cell membrane (e.g., Yoshikatsu Kanai, Protein, Nucleic Acid and Enzyme Vol. 46, No. 5, pp. 629-637, 2001 (Non-patent Document 1)).

Until now, many cases have been reported where the LAT1/CD98 complex is highly expressed in tumor cells (Yanagida et al., Biochimica et Biophysica Acta Vol. 1514, pp. 291-302, 2001 (Non-patent Document 2), Ohno et al., Cancer Sci. Vol. 99, No. 5, pp. 1000-1007, 2008 (Non-patent Document 3), Kaira et al., Cancer Sci. Vol. 99, No. 12, pp. 2380-2386, 2008 (Non-patent Document 4), Kaira et al., Cancer Sci. Vol. 100, No. 2, pp. 249-254, 2009 (Non-patent Document 5)). Amino acids are substances indispensable for cell growth, and tumor cells appear to require more amino acids than usual because they repeatedly grow in an uncontrolled manner. For this reason, it is inferred that the expression levels of amino acid transporters are higher in tumor cells than in normal cells. It is therefore suggested that the LAT1/CD98 complex is useful as a target molecule for tumor treatment.

CITATION LIST

Patent Documents

Patent Document 1: JP 2011-24537 A

Non-Patent Documents

Non-patent Document 1: Yoshikatsu Kanai, Protein, Nucleic Acid and Enzyme Vol. 46, No. 5, pp. 629-637, 2001
Non-patent Document 2: Yanagida et al., Biochimica et Biophysica Acta Vol. 1514, pp. 291-302, 2001
Non-patent Document 3: Ohno et al., Cancer Sci. Vol. 99, No. 5, pp. 1000-1007, 2008
Non-patent Document 4: Kaira et al., Cancer Sci. Vol. 99, No. 12, pp. 2380-2386, 2008
Non-patent Document 5: Kaira et al., Cancer Sci. Vol. 100, No. 2, pp. 249-254, 2009
Non-patent Document 6: Haynes et al., J Immunol. 1981 April; 126(4):1409-14.
Non-patent Document 7: Masuko et al., Jpn J Cancer Res. 1985 May; 76(5):386-94.

SUMMARY OF THE INVENTION

Problem to be Solved by the Invention

A monoclonal antibody which specifically binds to the LAT1/CD98 complex to inhibit its activity or induce cell damage is considered to be promising as a molecular targeted drug, but it should be an antibody recognizing the extracellular region of the LAT1/CD98 complex in terms of the properties required for antibody drugs. Until now, there have been reported some antibodies specifically recognizing CD98 (Haynes et al., J Immunol. 1981 April; 126(4):1409-14 (Non-patent Document 6); Masuko et al., Jpn J Cancer Res. 1985 May; 76(5):386-94 (Non-patent Document 7)), although there is only one report of an antibody recognizing the extracellular region of the LAT1/CD98 complex as an epitope (JP 2011-24537 A: Patent Document 1). However, the antibody disclosed in JP 2011-24537 A is not sufficient for practical use as an antitumor agent because its antibody titer is not high enough to treat humans.

Thus, there has been a demand for an antibody with higher performance as an antibody recognizing the extracellular region of the LAT1/CD98 complex as an epitope ("anti-LAT1/CD98 antibody").

Means to Solve the Problem

Under these circumstances, the present invention aims to provide a monoclonal antibody recognizing the extracellular region of the LAT1/CD98 complex, whose high expression is observed specifically in tumor cells, to inhibit the activity of the LAT1/CD98 complex or induce cytotoxic factors, thereby leading tumor cells to cell death. Further, the present invention aims to provide a hybridoma producing the antibody of the present invention, as well as a complex (immunoconjugate) formed between the antibody of the present invention and a compound with cell killing activity and/or antitumor activity or a radioisotope.

The inventors of the present invention have succeeded in preparing an anti-LAT1/CD98 antibody which has CDR amino acid sequences different from the amino acid sequences of CDRs in the anti-LAT1/CD98 antibody disclosed in JP 2011-24537 A and which has a significantly higher binding ability to the extracellular region of the LAT1/CD98 complex. Moreover, the inventors of the present invention have also confirmed that this antibody has significantly higher cell damage-inducing activity and internalization activity.

Thus, the present invention provides the following.

[1] An antibody or an antigen-binding fragment thereof, each specifically binding to the extracellular region of the LAT1/CD98 complex in LAT1/CD98-expressing cells, which is:

(1) an antibody or an antigen-binding fragment thereof, which comprises, as light chain complementarity determining region 1 (CDRL1), light chain complementarity determining region 2 (CDRL2) and light chain complementarity determining region 3 (CDRL3), the amino acid sequences of SEQ ID NO: 7, SEQ ID NO: 8 and SEQ ID NO: 9, respectively, or amino acid sequences modified to have mutation of one or several amino acid residues in the amino acid sequences of SEQ ID NO: 7, SEQ ID NO: 8 and SEQ ID NO: 9, respectively, and which comprises, as heavy chain complementarity determining region 1 (CDRH1), heavy chain complementarity determining region 2 (CDRH2) and heavy chain complementarity determining region 3 (CDRH3), the amino acid sequences of SEQ ID NO: 10, SEQ ID NO: 11 and SEQ ID NO: 12, respectively, or amino acid sequences modified to have mutation of one or several amino acid residues in the amino acid sequences of SEQ ID NO: 10, SEQ ID NO: 11 and SEQ ID NO: 12, respectively;

(2) an antibody or an antigen-binding fragment thereof, which comprises, as CDRL1, CDRL2 and CDRL3, the amino acid sequences of SEQ ID NO: 13, SEQ ID NO: 14 and SEQ ID NO: 15, respectively, or amino acid sequences modified to have mutation of one or several amino acid residues in the amino acid sequences of SEQ ID NO: 13, SEQ ID NO: 14 and SEQ ID NO: 15, respectively, and which comprises, as CDRH1, CDRH2 and CDRH3, the amino acid sequences of SEQ ID NO: 16, SEQ ID NO: 17 and SEQ ID NO: 18, respectively, or amino acid sequences modified to have mutation of one or several amino acid residues in the amino acid sequences of SEQ ID NO: 16, SEQ ID NO: 17 and SEQ ID NO: 18, respectively;

(3) an antibody or an antigen-binding fragment thereof, which comprises, as CDRL1, CDRL2 and CDRL3, the amino acid sequences of SEQ ID NO: 19, SEQ ID NO: 20 and SEQ ID NO: 21, respectively, or amino acid sequences modified to have mutation of one or several amino acid residues in the amino acid sequences of SEQ ID NO: 19, SEQ ID NO: 20 and SEQ ID NO: 21, respectively, and which comprises, as CDRH1, CDRH2 and CDRH3, the amino acid sequences of SEQ ID NO: 22, SEQ ID NO: 23 and SEQ ID NO: 24, respectively, or amino acid sequences modified to have mutation of one or several amino acid residues in the amino acid sequences of SEQ ID NO: 22, SEQ ID NO: 23 and SEQ ID NO: 24, respectively; or (4) an antibody or an antigen-binding fragment thereof, which comprises, as CDRL1, CDRL2 and CDRL3, the amino acid sequences of SEQ ID NO: 25, SEQ ID NO: 26 and SEQ ID NO: 27, respectively, or amino acid sequences modified to have mutation of one or several amino acid residues in the amino acid sequences of SEQ ID NO: 25, SEQ ID NO: 26 and SEQ ID NO: 27, respectively, and which comprises, as CDRH1, CDRH2 and CDRH3, the amino acid sequences of SEQ ID NO: 28, SEQ ID NO: 29 and SEQ ID NO: 30, respectively, or amino acid sequences modified to have mutation of one or several amino acid residues in the amino acid sequences of SEQ ID NO: 28, SEQ ID NO: 29 and SEQ ID NO: 30, respectively.

[2] An antibody or an antigen-binding fragment thereof, each specifically binding to the extracellular region of the LAT1/CD98 complex in LAT1/CD98-expressing cells, which comprises:

(1) light chain complementarity determining region 1 (CDRL1) comprising the amino acid sequence $X_1ASQX_2VGNNVA$ (SEQ ID NO: 1);

(2) light chain complementarity determining region 2 (CDRL2) comprising the amino acid sequence $YASX_3RX_4T$ (SEQ ID NO: 2);

(3) light chain complementarity determining region 3 (CDRL3) comprising the amino acid sequence $QRX_5YKSPYT$ (SEQ ID NO: 3), (4) heavy chain complementarity determining region 1 (CDRH1) comprising the amino acid sequence GFSLPTSSVS (SEQ ID NO: 4);

(5) heavy chain complementarity determining region 2 (CDRH2) comprising the amino acid sequence $VIWSNGNTDYSSX_6X_7KS$ (SEQ ID NO: 5); and (6) heavy chain complementarity determining region 3 (CDRH3) comprising the amino acid sequence $NFRNX_8PGVMDA$ (SEQ ID NO: 6) (provided that $X_1$ to $X_8$ are each any naturally occurring amino acid residue).

[3] The antibody or antigen-binding fragment thereof according to [2] above, wherein (SEQ ID NOS 39-43)
$X_1$ is R or K,
$X_2$ is N or T,
$X_3$ is S or N,
$X_4$ is H or N,
$X_5$ is V or I,
$X_6$ is A or R,
$X_7$ is I or F, and
$X_8$ is D or N.

[4] The antibody or antigen-binding fragment thereof according to [2] above, wherein

```
                                (SEQ ID NOS 7-9 and 11-12)
(1) X₁ is R, X₂ is N, X₃ is N, X₄ is N, X₅ is I, X₆ is A, X₇ is I, and X₈ is D, (SEQ ID NOS 13-15 and 17-18)
(2) X₁ is K, X₂ is N, X₃ is S, X₄ is H, X₅ is V, X₆ is R, X₇ is F, and X₈ is D, (SEQ ID NOS 19-21 and 23-24)
(3) X₁ is K, X₂ is T, X₃ is S, X₄ is H, X₅ is V, X₆ is R, X₇ is F, and X₈ is D,
or
                                (SEQ ID NOS 25-27 and 29-30)
(4) X₁ is K, X₂ is N, X₃ is S, X₄ IS H, X₅ is V, X₆ is R, X₇ is I, and X₈ is N.
```

[5] The antibody or antigen-binding fragment thereof according to any one of [1] to [4] above, which contains:
(1) a light chain variable region (VL) comprising an amino acid sequence sharing an identity of 90% or more with the amino acid sequence of SEQ ID NO: 31, and
a heavy chain variable region (VH) comprising an amino acid sequence sharing an identity of 90% or more with the amino acid sequence of SEQ ID NO: 32;
(2) a light chain variable region (VL) comprising an amino acid sequence sharing an identity of 90% or more with the amino acid sequence of SEQ ID NO: 33, and
a heavy chain variable region (VH) comprising an amino acid sequence sharing an identity of 90% or more with the amino acid sequence of SEQ ID NO: 34;
(3) a light chain variable region (VL) comprising an amino acid sequence sharing an identity of 90% or more with the amino acid sequence of SEQ ID NO: 35, and
a heavy chain variable region (VH) comprising an amino acid sequence sharing an identity of 90% or more with the amino acid sequence of SEQ ID NO: 36; or
(4) a light chain variable region (VL) comprising an amino acid sequence sharing an identity of 90% or more with the amino acid sequence of SEQ ID NO: 37, and
a heavy chain variable region (VH) comprising an amino acid sequence sharing an identity of 90% or more with the amino acid sequence of SEQ ID NO: 38.
[6] The antibody or antigen-binding fragment thereof according to any one of [1] to [5] above, which contains:
(1) a light chain variable region (VL) comprising the amino acid sequence of SEQ ID NO: 31, and
a heavy chain variable region (VH) comprising the amino acid sequence of SEQ ID NO: 32;
(2) a light chain variable region (VL) comprising the amino acid sequence of SEQ ID NO: 33, and
a heavy chain variable region (VH) comprising the amino acid sequence of SEQ ID NO: 34;
(3) a light chain variable region (VL) comprising the amino acid sequence of SEQ ID NO: 35, and
a heavy chain variable region (VH) comprising the amino acid sequence of SEQ ID NO: 36; or
(4) a light chain variable region (VL) comprising the amino acid sequence of SEQ ID NO: 37, and
a heavy chain variable region (VH) comprising the amino acid sequence of SEQ ID NO: 38.
[7] The antibody or antigen-binding fragment thereof according to any one of [1] to [6] above, which has cytotoxic activity and/or internalization activity on LAT1/CD98-expressing cells.
[8] The antibody or antigen-binding fragment thereof according to any one of [1] to [7] above, whose subclass is IgG.
[9] The antibody or antigen-binding fragment thereof according to [8] above, wherein the IgG is $IgG_{2a}$ or $IgG_1$.
[10] The antibody or antigen-binding fragment thereof according to any one of [1] to [9] above, wherein the antigen-binding fragment is any of Fab, Fab', $F(ab')_2$, scFv, dsFv, ds-scFv, dimers, minibodies, diabodies and multimers thereof, or a bispecific antibody fragment.
[11] The antibody or antigen-binding fragment thereof according to any one of [1] to [10] above, which is a monoclonal antibody.
[12] The antibody or antigen-binding fragment thereof according to any one of [1] to [11] above, which is a rat, mouse, primate or human antibody.
[13] The antibody or antigen-binding fragment thereof according to any one of [1] to [11] above, which is a chimeric antibody or a humanized antibody.
[14] An immunoconjugate, which comprises the antibody or antigen-binding fragment thereof according to any one of [1] to [13] above and at least one cytotoxic drug, antitumor agent or radioisotope.
[15] An isolated nucleic acid molecule, which encodes the antibody or antigen-binding fragment thereof according to any one of [1] to [14] above.
[16] An expression vector, which comprises the nucleic acid molecule according to [15] above.
[17] A hybridoma cell or a transgenic cell, each producing the antibody according to any one of [1] to [13] above, which comprises the nucleic acid molecule according to [15] above or is transformed with the nucleic acid molecule.
[18] A method for preparation of a monoclonal antibody specifically binding to the extracellular region of the LAT1/CD98 complex, which comprises culturing the cell according to [17] above and collecting an antibody specifically binding to the LAT1/CD98 complex from the resulting cultured product.
[19] A method for preparation of a monoclonal antibody specifically binding to the extracellular region of LAT1/CD98, which comprises isolating a gene encoding an anti-LAT1/CD98 monoclonal antibody from the cell according to [17] above, constructing an expression vector comprising the gene, introducing the expression vector into a host to cause expression of the monoclonal antibody, and collecting the monoclonal antibody specifically binding to the extracellular region of LAT1/CD98 from the resulting host, the culture supernatant of the host or the secretory product of the host.
[20] The method for preparation according to [19] above, wherein the host is *E. coli*, a yeast cell, an insect cell, a mammalian cell, a plant cell or a mammal
[21] A composition containing the antibody or antigen-binding fragment thereof or immunoconjugate thereof according to any one of [1] to [14] above, which is used for induction of apoptosis by being applied to LAT1/CD98-expressing cells.
[22] A pharmaceutical preparation for prevention or treatment of tumor, which contains the antibody or antigen-binding fragment thereof or immunoconjugate thereof according to any one of [1] to [14] above.
[23] A composition containing the antibody or antigen-binding fragment thereof or immunoconjugate thereof according to any one of [1] to [14] above, which is used for detection of LAT1/CD98-expressing cells.
[24] A method for detection of tumor, which comprises reacting the composition according to [23] above with a sample taken from a living organism and detecting the reacted signals.
[25] A method for in vitro immunological detection of tumor, which comprises the step of contacting the composition according to [23] above with cancer cells.
[26] A method for in vivo imaging of tumor, which comprises the steps of administering the composition according to [23] above to a subject and obtaining a detection image by near-infrared optical imaging, PET, MRI or ultrasonic imaging.
[27] A pharmaceutical preparation for diagnosis of tumor, which contains the antibody or antigen-binding fragment thereof or immunoconjugate thereof according to any one of [1] to [14] above.
[28] The pharmaceutical preparation according to [22] or [27] above, wherein the tumor is at least one selected from the group consisting of colorectal cancer, colon and rectal cancer, lung cancer, breast cancer, brain tumor, melanoma, renal cell carcinoma, bladder cancer, leukemia, lymphoma, T cell lymphoma, multiple myeloma, gastric cancer, pancreatic cancer, uterine cervical cancer, endometrial cancer, ovarian cancer, esophageal cancer, liver cancer, head and neck squamous cell carcinoma, skin cancer, urinary tract cancer, prostate cancer, choriocarcinoma, pharyngeal cancer, laryngeal cancer, tongue cancer, oral cancer, gallbladder cancer, thyroid cancer, mesothelioma, pleural tumor, arrhenoblastoma, endometrial hyperplasia, endometriosis, embryoma, fibrosarcoma, Kaposi's sarcoma, hemangioma, cavernous hemangioma, hemangioblastoma, retinoblastoma, astrocytoma, neurofibroma, oligodendroglioma, medulloblastoma, neuroblastoma, neuroglioma, rhabdomyosarcoma, glioblastoma, osteogenic sarcoma, leiomyosarcoma, thyroid sarcoma, and Wilms tumor.

[29] A complementarity determining region (CDR), which is selected from the group consisting of (1) to (6) shown below:

(1) light chain complementarity determining region 1 (CDRL1) comprising the amino acid sequence of SEQ ID NO: 7, 13, 19 or 25;

(2) light chain complementarity determining region 2 (CDRL2) comprising the amino acid sequence of SEQ ID NO: 8, 14, 20 or 26;

(3) light chain complementarity determining region 3 (CDRL3) comprising the amino acid sequence of SEQ ID NO: 9, 15, 21 or 27;

(4) heavy chain complementarity determining region 1 (CDRH1) comprising the amino acid sequence of SEQ ID NO: 10, 16, 22 or 28;

(5) heavy chain complementarity determining region 2 (CDRH2) comprising the amino acid sequence of SEQ ID NO: 11, 17, 23 or 29; and (6) heavy chain complementarity determining region 3 (CDRH3) comprising the amino acid sequence of SEQ ID NO: 12, 18, 24 or 30.

[30] A chimeric antigen receptor (CAR) comprising the heavy chain variable region (VH) and the light chain variable region (VL) as defined in (1), (2), (3) or (4) of [5] or [6] above.

[31] A genetically modified T cell having the CAR according to [30] above being expressed on its surface (CAR-T cell).

[32] A method for treatment of cancer comprising the steps of contacting the genetically engineered T cell (CAR-T cell) according to [31] above with a cancer cell of a patient, and inducing apoptosis of the cancer cell.

[33] A pharmaceutical composition for treatment of cancer comprising the genetically engineered T cell (CAR-T cell) according to [31] above and a pharmaceutically acceptable carrier.

Advantageous Effects of the Invention

The antibody of the present invention or an antigen-binding fragment thereof specifically recognizes the extracellular region of the LAT1/CD98 complex to inhibit the activity of the LAT1/CD98 complex or induce cytotoxic factors in cells expressing the LAT1/CD98 complex, thereby causing cell death in these cells. Moreover, an immunoconjugate formed between the antibody of the present invention or an antigen-binding fragment thereof and a compound with cell killing activity and/or antitumor activity or a radioisotope can cause cell death in cells expressing the LAT1/CD98 complex. Due to its ability to specifically recognize the extracellular region of the LAT1/CD98 complex, the antibody of the present invention or an antigen-binding fragment thereof is particularly useful as an anticancer antibody drug. The present invention provides a particularly advantageous effect over the previously reported antibody capable of specifically recognizing the extracellular region of the LAT1/CD98 complex.

DESCRIPTION OF EMBODIMENTS

Figure 1:
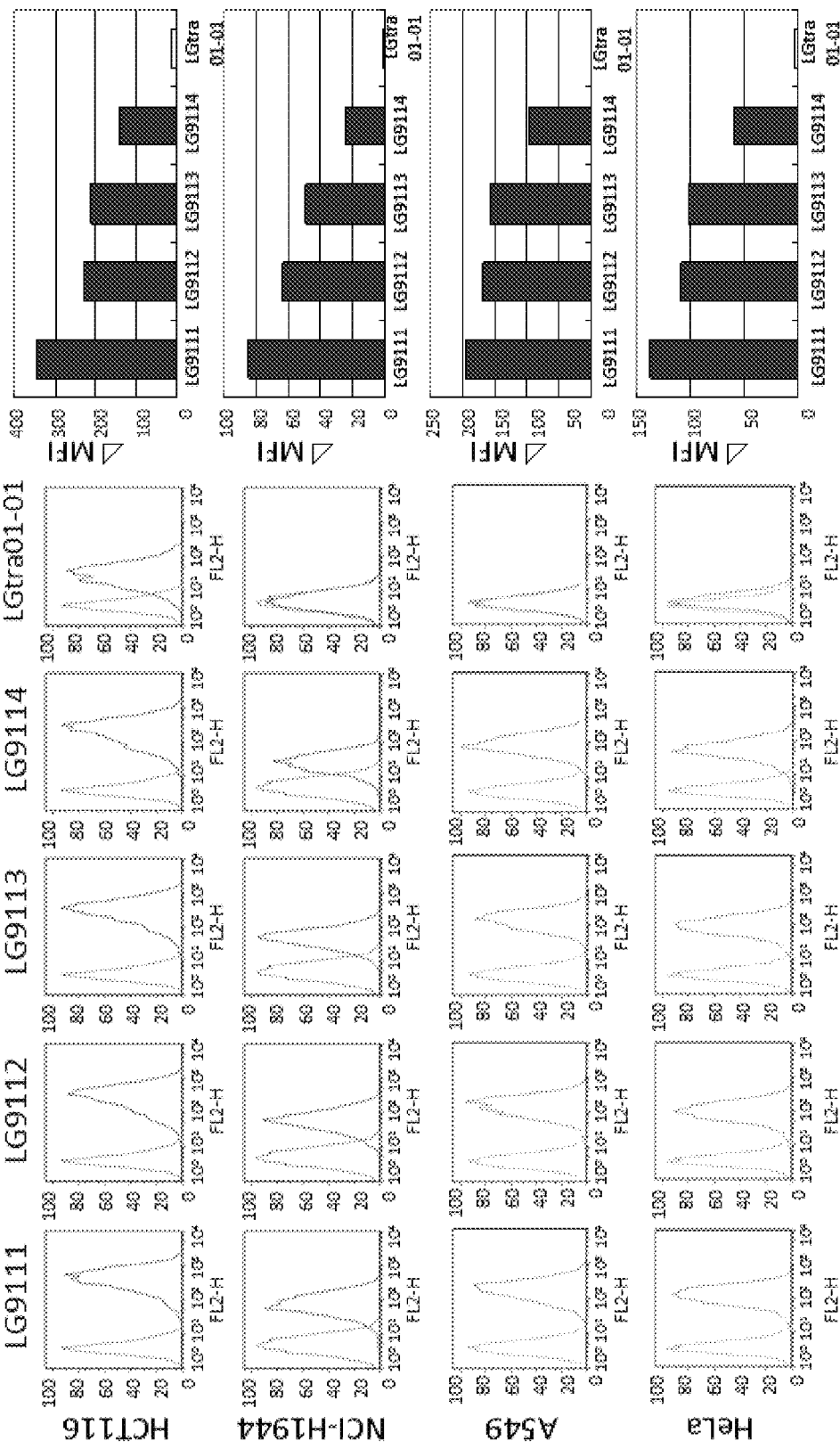
FIG. 1(A) shows the binding ability of monoclonal antibodies LG9111, LG9112, LG9113, LG9114 and LGtra01-01 to human colorectal cancer cell line (HCT116), human lung cancer cell lines (NCI-H1944, A549) and human uterine cervical cancer cell line (HeLa). The red lines represent histograms obtained for reaction with the respective monoclonal antibodies, while the blue line represents a histogram obtained for reaction with rat IgG as a control.
FIG. 1(B) shows in graph format the histograms shown in (A). Data is expressed as a value (ΔMFI) calculated by subtracting the MFI (mean fluorescence intensity) of the control from the MFI upon reaction with each antibody.

1. Antibody Specifically Recognizing the Extracellular Region of the LAT1/CD98 Complex In one embodiment, the present invention provides an antibody specifically binding to the extracellular region of the LAT1/CD98 complex (which is also herein referred to as "anti-LAT1/CD98 antibody") or an antigen-binding fragment thereof. Namely, the present invention provides an antibody or an antigen-binding fragment thereof, each recognizing a part or the whole of the amino acid sequence of the extracellular region of the LAT1/CD98 complex as an epitope.

The first isoform of the amino acid transport system L, i.e., "human LAT1 (L-type amino acid transporter 1)" is a twelve-transmembrane type membrane protein composed of 507 amino acid residues. Information such as the amino acid sequence and mRNA sequence of human LAT1 can be obtained under Accession numbers such as AAD20464 and AF104032, respectively, from GenBank or other publicly accessible databases. Likewise, mouse or other mammalian (e.g., rat, bovine) LAT1 can also be obtained from publicly accessible databases.

"Human CD98" which forms a complex with human LAT1 on the cell membrane is a single transmembrane type II membrane protein composed of 630 amino acid residues. Information such as the amino acid sequence and mRNA sequence of human CD98 can be obtained under Accession numbers such as NP_002385 and NM_002394, respectively, from GenBank or other publicly accessible databases. Likewise, mouse or other mammalian (e.g., rat, bovine) CD98 can also be obtained from publicly accessible databases.

When herein simply referred to as "LAT1/CD98," it is intended to mean the LAT1/CD98 complex protein. In some cases, the respective genes encoding the LAT1 protein and the CD98 protein (or simply the LAT1 gene and the CD98 gene) are simply referred to as LAT1 and CD98, although it would be obvious to those skilled in the art that they refer to the LAT1 gene and the CD98 gene, respectively, in light of the context. LAT1 and CD98 are typically intended herein to mean human LAT1 and human CD98, but they may be non-human mammalian (e.g., mouse, rat, bovine) LAT1 and CD98.

As used herein, the phrase "extracellular region of LAT1/CD98" is intended to mean, when LAT1/CD98 is expressed on the cell surface, a region of LAT1/CD98 exposed on the cell surface at the side of the cell membrane not facing the cytoplasm (i.e., at the outer side of the cell). Whether or not the antibody of the present invention or an antigen-binding fragment thereof binds to the extracellular region of LAT1/CD98 can be confirmed, for example, by FCM analysis (FCM is an abbreviation of flow cytometry) with the use of human tumor cell lines, as described herein in Example 2. It should be noted that regions covering amino acid residues at positions 71 to 83, amino acid residues at positions 141 to 145, amino acid residues at positions 191 to 198, amino acid residues at positions 264 to 273, amino acid residues at positions 340 to 395, and amino acid residues at positions 452 to 457 have each been predicted as an extracellular region of LAT1 from its amino acid sequence in publicly accessible databases (e.g., UniProt).

When used herein to describe an antibody or an antigen-binding fragment thereof, the phrase "specifically binding to" the extracellular region of LAT1/CD98 is intended to mean that the antibody or antigen-binding fragment thereof binds to a specific amino acid sequence in these regions with a substantially higher affinity than that for other amino acid sequences. The phrase "substantially higher affinity" used here is intended to mean an affinity that is high enough to detect the specific amino acid sequence as distinguished from other amino acid sequences, as measured with a desired measuring device, and it is typically intended to mean binding affinity with a binding constant ($K_a$) of at least $10^7$ M$^{-1}$, preferably at least $10^8$ M$^{-1}$, more preferably $10^9$ M$^{-1}$, and even more preferably $10^{10}$ M$^{-1}$, $10^{11}$ M$^{-1}$, $10^{12}$ M$^{-1}$ or higher, e.g., $10^{13}$ M$^{-1}$ or higher at the maximum.

As used herein, the term "antibody" is intended to include all classes and subclasses of intact immunoglobulins. The antibody of the present invention is preferably of IgG subclass, more preferably of human IgG$_1$ subclass. The "antibody" intended here particularly includes monoclonal antibodies.

As used herein, the term "antigen-binding fragment" is intended to mean a fragment having an antigen-binding region or a variable region from an intact and/or humanized and/or chimeric antibody, and examples include Fab, Fab', F(ab')$_2$, Fv and ScFv fragments of the above antibodies. Such fragments have been conventionally prepared by proteolysis (e.g., papain digestion) of intact antibodies (see, e.g., WO94/29348), but they can also be directly produced from transformed host cells by gene recombination. For preparation of ScFv, it is possible to use the method described in Bird et al., (1988) Science, 242, 423-426. Further, antibody fragments can also be prepared by using various genetic engineering techniques described below.

Fv fragments appear to have lower interaction energy of their two chains than Fab fragments. To stabilize binding between VH and VL domains, these domains are linked via peptides (Bird et al., (1988) Science 242, 423-426, Huston et al., PNAS, 85, 5879-5883), disulfide bridges (Glockshuber et al., (1990) Biochemistry, 29, 1362-1367) and "knob in hole" mutations (Zhu et al., (1997), Protein Sci., 6, 781-788). ScFv fragments can be prepared in a manner well known to those skilled in the art (see Whitlow et al., (1991) Methods companion Methods Enzymol, 2, 97-105 and Huston et al., (1993) Int. Rev. Immunol 10, 195-217). ScFv can be produced within bacterial cells such as *E. coli*, but is more preferably produced within eukaryotic cells. Disadvantages of ScFv are the monovalency of the product, which can preclude an increased avidity due to polyvalent binding, as well as its short half-life. Attempts to overcome these problems include bivalent (ScFv')$_2$, which is produced from ScFv containing an additional C-terminal cysteine by chemical coupling (Adams et al., (1993) Can. Res 53, 4026-4034 and McCartney et al., (1995) Protein Eng. 8, 301-314) or by spontaneous site-specific dimerization of ScFv containing an unpaired C-terminal cysteine residue (see Kipriyanov et al., (1995) Cell. Biophys 26, 187-204). Alternatively, ScFv can be forced to form multimers by shortening the peptide linker to 3 to 12 residues to form "diabodies." See Holliger et al., PNAS (1993), 90, 6444-6448. Reducing the linker still further can result in ScFv trimers ("triabodies"; see Kortt et al., (1997) Protein Eng, 10, 423-433) and tetramers ("tetrabodies"; see Le Gall et al., (1999) FEBS Lett, 453, 164-168). Construction of bivalent ScFv molecules can also be achieved by gene fusion with protein dimerizing motifs to form "miniantibodies" (see Pack et al., (1992) Biochemistry 31, 1579-1584) and "minibodies" (see Hu et al., (1996), Cancer Res. 56, 3055-3061). ScFv-ScFv tandems ((ScFv)$_2$) can also be prepared by linking two ScFv units via a third peptide linker (see Kurucz et al., (1995) J. Immol 154, 4576-4582). Bispecific diabodies can be prepared through non-covalent bonding between two single chain fusion products consisting of the VH domain from one antibody connected via a short linker to the VL domain of another antibody (see Kipriyanov et al., (1998), Int. J. Can 77, 763-772). The stability of such bispecific diabodies can be enhanced by introduction of disulfide bridges or "knob in hole" mutations as described above or by formation of single chain diabodies (ScDb) where two hybrid ScFv fragments are connected via a peptide linker (see Kontermann et al., (1999) J. Immol. Methods 226 179-188). Tetravalent bispecific molecules can be obtained, for example, by fusion of an ScFv fragment to the CH3 domain of an IgG molecule or to a Fab fragment through the hinge region (see Coloma et al., (1997) Nature Biotechnol. 15, 159-163). Alternatively, tetravalent bispecific molecules have been prepared by fusion of bispecific single chain diabodies (see Alt et al., (1999) FEBS Lett 454, 90-94). Smaller tetravalent bispecific molecules can also be prepared either by dimerization of ScFv-ScFv tandems via a linker containing a helix-loop-helix motif (DiBi miniantibodies; see Muller et al., (1998) FEBS Lett 432, 45-49) or by dimerization of a single chain molecule comprising four antibody variable domains (VH and VL) in an orientation preventing intramolecular pairing (tandem diabody; see Kipriyanov et al., (1999) J. Mol. Biol. 293, 41-56). Bispecific F(ab')$_2$ fragments can be prepared by chemical coupling of Fab' fragments or by heterodimerization through leucine zippers (see Shalaby et al., (1992) J. Exp. Med. 175, 217-225 and Kostelny et al., (1992), J. Immunol. 148, 1547-1553). Moreover, isolated VH and VL domains (Domantis plc) are also available for use.

As used herein, the term "monoclonal antibody" refers to an antibody (or an antibody fragment) obtained from a population of substantially homogeneous antibodies, i.e., the individual antibodies constituting the population are identical with each other, except for possible naturally occurring mutations that may be present in minor amounts. Monoclonal antibodies are highly specific and directed against a single antigenic site. In contrast to polyclonal antibody preparations which typically include different antibodies directed against different determinants (epitopes), each monoclonal antibody is directed against a single determinant on the antigen. In addition to their specificity, monoclonal antibodies are advantageous in that they are synthesized by hybridoma culture and are not contaminated with other immunoglobulins. The modifier "monoclonal" indicates the character of the antibody as being obtained from a population of substantially homogeneous antibodies, and is not to be construed as requiring production of the antibody by any particular method. For example, the monoclonal antibodies to be used in accordance with the present invention may be prepared by the hybridoma method first described by Kohler et al., Nature, 256: 495 [1975] or may be prepared by recombinant DNA techniques (see, e.g., U.S. Pat. No. 4,816,567). Moreover, the "monoclonal antibodies" intended here also include clones of antigen recognition and binding site containing antibody fragments (Fv clones) isolated from phage antibody libraries by using the techniques described in Clackson et al., Nature, 352: 624-628 [1991] and Marks et al., J. Mol. Biol., 222: 581-597 (1991), by way of example.

The "monoclonal antibodies" intended here include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they show the desired biological activity (Morrison et al., Proc. Natl. Acad. Sci. USA, 81: 6851-6855 [1984]).

"Humanized" forms of non-human (e.g., mouse) antibodies are chimeric immunoglobulins, immunoglobulin chains or fragments thereof (e.g., Fv, Fab, Fab', F(ab')$_2$ or other antigen-binding subsequences of antibodies) which contain a minimal sequence derived from a non-human immunoglobulin. For the most part, humanized antibodies are human immunoglobulins (recipient antibody) in which residues from a CDR of the recipient are replaced with residues from a CDR of a non-human species (donor antibody) such as mouse, rat, rabbit, primate (e.g., monkey) having the desired specificity, affinity and capacity. In some cases, Fv framework region (FR) residues of the human immunoglobulin are replaced with corresponding non-human residues. Furthermore, the humanized antibody may comprise residues which are found neither in the recipient antibody nor in the imported CDR or framework sequences. These modifications are made to further refine and optimize antibody performance. In general, the humanized antibody may comprise substantially all of at least one, and typically two, variable domains, in which all or substantially all of the CDR regions correspond to those of a non-human immunoglobulin and all or substantially all of the FR regions are those of a human immunoglobulin sequence. The most suitable humanized antibody may also comprise at least a portion of an immunoglobulin constant region (Fc), typically that of a human immunoglobulin.

As used herein, the phrase "activity of LAT1/CD98" refers to neutral amino acid transport activity, amino acid analogue drug transport activity, etc. The amino acid transport activity of LAT1/CD98 may be measured, for example, by intracellular uptake of labeled amino acids. The phrase "inhibit the activity of LAT1/CD98" is intended to mean significantly reducing or eliminating the activities of LAT1/CD98 mentioned above. The phrase "significantly reducing or eliminating the activities of LAT1/CD98" is intended to mean causing at least a 5% or more reduction in the biological activities of LAT1/CD98.

As used herein, the term "cytotoxic activity" refers to the ability to cause cell damage in cells, and when used in the context of the present invention, it is intended to mean the ability to induce cytotoxic factors and thereby cause cell death or apoptosis in LAT1/CD98-expressing cells when the antibody of the present invention or an antigen-binding fragment thereof specifically binds to these cells. The cytotoxic activity may be evaluated as a cytotoxic rate by being measured in the manner described in Example 2 of the present invention, by way of example.

As used herein, the term "cell death" refers to "apoptosis." "Apoptosis" is a common type of functional and active cell death induced by various physiological and pathological factors such as ontogenetic program, death factor stimulation, radiation-induced severe damage to chromosomal DNA, abnormal protein accumulation-induced severe stress in recipients, etc. In contrast to necrosis associated with cytoplasmic and nuclear swelling, apoptosis causes cytoplasmic and nuclear condensation and fragmentation.

The antibody of the present invention or an antigen-binding fragment thereof may be exemplified by an antibody or an antigen-binding fragment thereof, each specifically binding to the extracellular region of the LAT1/CD98 complex in LAT1/CD98-expressing cells, which comprises at least one of:

(1) light chain complementarity determining region 1 (CDRL1) comprising the amino acid sequence of SEQ ID NO: 1;

(2) light chain complementarity determining region 2 (CDRL2) comprising the amino acid sequence of SEQ ID NO: 2;

(3) light chain complementarity determining region 3 (CDRL3) comprising the amino acid sequence of SEQ ID NO: 3;

(4) heavy chain complementarity determining region 1 (CDRH1) comprising the amino acid sequence of SEQ ID NO: 4;

(5) heavy chain complementarity determining region 2 (CDRH2) comprising the amino acid sequence of SEQ ID NO: 5; and (6) heavy chain complementarity determining region 3 (CDRH3) comprising the amino acid sequence of SEQ ID NO: 6.

As used herein, the phrase "mutation of one or several amino acid residues" is intended to mean deletion, substitution, insertion or addition of one or several (e.g., 2, 3, 4 or 5) amino acid residues in the original amino acid sequence. Due to the presence of such a mutation, the subject amino acid sequence will be able to share an identity (%) of 90% or more, 91% or more, 92% or more, 93% or more, 94% or more, 95% or more, 96% or more, 97% or more, 98% or more, or 99% or more with the original amino acid sequence. In the context of the present invention, an antibody or an antigen-binding fragment thereof, each having an amino acid sequence comprising such a mutation at a corresponding position in the original amino acid sequence, has biological activities comparable to those of an antibody or an antigen-binding fragment thereof, each having the original amino acid sequence. The "biological activities comparable to" intended here include (i) the ability to bind with specificity to an antigen to which the antibody or antigen-binding fragment thereof having the original amino acid sequence specifically binds, (ii) the ability to inhibit the amino acid transport activity of LAT1/CD98, (iii) cytotoxic activity against LAT1/CD98-expressing cells upon binding to LAT1/CD98 on these cells, or (iv) any two or more or all of these activities. Most preferably, the phrase "biological activities comparable to" has the meaning in (iv) above. Moreover, the upper limit of the number of mutated amino acid residues in the above phrase "mutation of one or several amino acid residues" is limited by criteria of whether or not such comparable specificity can be maintained.

In general, amino acids constituting naturally occurring proteins can be grouped depending on the properties of their side chains. For example, they may be divided into groups of amino acids having similar properties, e.g., a group of aromatic amino acids (tyrosine, phenylalanine, tryptophan), a group of basic amino acids (lysine, arginine, histidine), a group of acidic amino acids (aspartic acid, glutamic acid), a group of neutral amino acids (serine, threonine, asparagine, glutamine), a group of amino acids with hydrocarbon chains (alanine, valine, leucine, isoleucine, proline), and a group of other amino acids (glycine, methionine, cysteine).

Examples of interchangeable amino acid residues including unnatural amino acids are as shown below. Amino acid residues included in the same group are interchangeable with each other. Group A: leucine, isoleucine, norleucine, valine, norvaline, alanine, 2-aminobutanoic acid, methionine, o-methylserine, t-butylglycine, t-butylalanine, cyclohexylalanine; Group B: aspartic acid, glutamic acid, isoaspartic acid, isoglutamic acid, 2-aminoadipic acid, 2-aminosuberic acid; Group C: asparagine, glutamine; Group D: lysine, arginine, ornithine, 2,4-diaminobutanoic acid, 2,3-diaminopropionic acid; Group E: proline, 3-hydroxyproline, 4-hydroxyproline; Group F: serine, threonine, homoserine; Group G: phenylalanine, tyrosine, tryptophan.

It should be noted that the identity of amino acid sequences or nucleotide sequences can be determined by using the algorithm of Karlin and Altschul, BLAST (PNAS, 1990 (vol. 87) p. 2264; PNAS, 1993 (vol. 90) p. 5873). Based on the algorithm of BLAST, programs called BLASTN and BLASTX have been developed (J Mol Biol, 1990 (vol. 215) p. 403). If BLASTN is used for nucleotide sequence analysis, parameters may be set to, for example, score=100 and wordlength=12. Likewise, if BLASTX is used for amino acid sequence analysis, parameters may be se to, for example, score=50 and wordlength=3. If BLAST and Gapped BLAST programs are used, default parameters in each program may be used. Alternatively, to determine the identity of amino acid sequence between proteins, the amino acid sequences of two proteins to be compared may be aligned to visually count amino acid residues matched between the proteins, followed by calculation according to the formula "(the number of matched amino acid residues/the number of amino acid residues in the entire protein)×100(%)."

The antibody of the present invention or an antigen-binding fragment thereof may preferably be exemplified by:

(1) an antibody or an antigen-binding fragment thereof, each specifically binding to the extracellular region of the LAT1/CD98 complex in LAT1/CD98-expressing cells, which comprises, as light chain complementarity determining region 1 (CDRL1), light chain complementarity determining region 2 (CDRL2) and light chain complementarity determining region 3 (CDRL3), the amino acid sequences of SEQ ID NO: 7, SEQ ID NO: 8 and SEQ ID NO: 9, respectively, or amino acid sequences modified to have mutation of one or several amino acid residues in the amino acid sequences of SEQ ID NO: 7, SEQ ID NO: 8 and SEQ ID NO: 9, respectively, and which comprises, as heavy chain complementarity determining region 1 (CDRH1), heavy chain complementarity determining region 2 (CDRH2) and heavy chain complementarity determining region 3 (CDRH3), the amino acid sequences of SEQ ID NO: 10, SEQ ID NO: 11 and SEQ ID NO: 12, respectively, or amino acid sequences modified to have mutation of one or several amino acid residues in the amino acid sequences of SEQ ID NO: 10, SEQ ID NO: 11 and SEQ ID NO: 12, respectively;

(2) an antibody or an antigen-binding fragment thereof, each specifically binding to the extracellular region of the LAT1/CD98 complex in LAT1/CD98-expressing cells, which comprises, as CDRL1, CDRL2 and CDRL3, the amino acid sequences of SEQ ID NO: 13, SEQ ID NO: 14 and SEQ ID NO: 15, respectively, or amino acid sequences modified to have mutation of one or several amino acid residues in the amino acid sequences of SEQ ID NO: 13, SEQ ID NO: 14 and SEQ ID NO: 15, respectively, and which comprises, as CDRH1, CDRH2 and CDRH3, the amino acid sequences of SEQ ID NO: 16, SEQ ID NO: 17 and SEQ ID NO: 18, respectively, or amino acid sequences modified to have mutation of one or several amino acid residues in the amino acid sequences of SEQ ID NO: 16, SEQ ID NO: 17 and SEQ ID NO: 18, respectively;

(3) an antibody or an antigen-binding fragment thereof, each specifically binding to the extracellular region of the LAT1/CD98 complex in LAT1/CD98-expressing cells, which comprises, as CDRL1, CDRL2 and CDRL3, the amino acid sequences of SEQ ID NO: 19, SEQ ID NO: 20 and SEQ ID NO: 21, respectively, or amino acid sequences modified to have mutation of one or several amino acid residues in the amino acid sequences of SEQ ID NO: 19, SEQ ID NO: 20 and SEQ ID NO: 21, respectively, and which comprises, as CDRH1, CDRH2 and CDRH3, the amino acid sequences of SEQ ID NO: 22, SEQ ID NO: 23 and SEQ ID NO: 24, respectively, or amino acid sequences modified to have mutation of one or several amino acid residues in the amino acid sequences of SEQ ID NO: 22, SEQ ID NO: 23 and SEQ ID NO: 24, respectively; or (4) an antibody or an antigen-binding fragment thereof, each specifically binding to the extracellular region of the LAT1/CD98 complex in LAT1/CD98-expressing cells, which comprises, as CDRL1, CDRL2 and CDRL3, the amino acid sequences of SEQ ID NO: 25, SEQ ID NO: 26 and SEQ ID NO: 27, respectively, or amino acid sequences modified to have mutation of one or several amino acid residues in the amino acid sequences of SEQ ID NO: 25, SEQ ID NO: 26 and SEQ ID NO: 27, respectively, and which comprises, as CDRH1, CDRH2 and CDRH3, the amino acid sequences of SEQ ID NO: 28, SEQ ID NO: 29 and SEQ ID NO: 30, respectively, or amino acid sequences modified to have mutation of one or several amino acid residues in the amino acid sequences of SEQ ID NO: 28, SEQ ID NO: 29 and SEQ ID NO: 30, respectively.

Alternatively, the antibody of the present invention or an antigen-binding fragment thereof may preferably be exemplified by an antibody or an antigen-binding fragment thereof, each specifically binding to the extracellular region of the LAT1/CD98 complex in LAT1/CD98-expressing cells, which contains:

(1) a light chain variable region (VL) comprising an amino acid sequence sharing an identity of 90% or more with the amino acid sequence of SEQ ID NO: 31, and
a heavy chain variable region (VH) comprising an amino acid sequence sharing an identity of 90% or more with the amino acid sequence of SEQ ID NO: 32;

(2) a light chain variable region (VL) comprising an amino acid sequence sharing an identity of 90% or more with the amino acid sequence of SEQ ID NO: 33, and
a heavy chain variable region (VH) comprising an amino acid sequence sharing an identity of 90% or more with the amino acid sequence of SEQ ID NO: 34;

(3) a light chain variable region (VL) comprising an amino acid sequence sharing an identity of 90% or more with the amino acid sequence of SEQ ID NO: 35, and
a heavy chain variable region (VH) comprising an amino acid sequence sharing an identity of 90% or more with the amino acid sequence of SEQ ID NO: 36; or (4) a light chain variable region (VL) comprising an amino acid sequence sharing an identity of 90% or more with the amino acid sequence of SEQ ID NO: 37, and
a heavy chain variable region (VH) comprising an amino acid sequence sharing an identity of 90% or more with the amino acid sequence of SEQ ID NO: 38.

It should be noted that the above percentage of identity may be, in more detail, 90%, 91%, 92%, 93%, 94%, 95%, 96%, 97%, 98%, 99% or 100%.

2. Nucleic Acid Encoding the Antibody of the Present Invention

In another embodiment, the present invention provides an isolated nucleic acid molecule, which encodes an antibody or an antigen-binding fragment thereof, each specifically binding to the extracellular region of LAT1/CD98. Such a nucleic acid molecule may be either RNA or DNA. The nucleic acid molecule of the present invention can be used to prepare the antibody of the present invention or an antigen-binding fragment thereof Thus, in another related embodiment of the present invention, there is provided a method for preparation of a monoclonal antibody specifically binding to the extracellular region of LAT1/CD98, which comprises isolating a gene encoding an anti-LAT1/CD98 monoclonal antibody from the hybridoma cells of the present invention, constructing an expression vector comprising the gene, introducing the expression vector into a host to cause expression of the monoclonal antibody, and collecting the monoclonal antibody specifically binding to the extracellular region of LAT1/CD98 from the resulting host, the culture supernatant of the host or the secretory product of the host.

DNA encoding the antibody of the present invention or an antigen-binding fragment thereof may be easily separated in a standard manner (e.g., with the use of oligonucleotide probes capable of specifically binding to genes encoding mouse antibody heavy and light chains) and then sequenced. Hybridoma cells producing monoclonal antibodies serve as a preferred source for such DNA. For monoclonal antibody synthesis in recombinant host cells, DNA once separated may be inserted into an expression vector, which may then be transfected into host cells such as E. coli cells, human HEK293 fetal kidney-derived cells, monkey COS cells, Chinese hamster ovary (CHO) cells or myeloma cells, which do not otherwise produce antibody proteins. This DNA may be modified, for example, by replacing homologous mouse sequences with sequences for human heavy and light chain constant domains (Morrison et al., Proc. Natl. Acad. Sci., USA, 81:6851[1984]) or by covalently joining the whole or part of the coding sequence for a non-immunoglobulin polypeptide to the immunoglobulin coding sequence. "Chimeric" or "hybrid" antibodies are prepared such that they have the binding specificity of the anti-LAT1/CD98 monoclonal antibody of the present invention.

3. Hybridoma Cells Producing the Antibody of the Present Invention

In yet another embodiment, the present invention provides hybridoma cells producing an antibody or an antigen-binding fragment thereof, each specifically binding to the extracellular region of LAT1/CD98. The present invention also provides a hybridoma containing a nucleic acid molecule encoding an antibody or an antigen-binding fragment thereof, each specifically binding to the extracellular region of LAT1/CD98.

The hybridoma cells of the present invention may be prepared as follows in more detail, but not limited thereto.

(1) Preparation of Antigen

As an antigen required for preparation of the anti-LAT1/CD98 monoclonal antibody, it is possible to use LAT1/CD98-producing cells or a cell fraction thereof, etc.

(2) Immunization of Animals and Preparation of Antibody-Producing Cells

Mice or rats at 6 to 24 weeks of age are immunized with the antigen prepared in the manner shown in (1) to collect antibody-producing cells from their spleens, lymph nodes and/or peripheral blood. For immunization, the antigen is administered to the animals subcutaneously, intravenously or intraperitoneally, together with an appropriate adjuvant [e.g., Freund's complete adjuvant or aluminum hydroxide gel and pertussis vaccine, etc.]. Administration of the antigen is repeated 3 to 7 times every 2 to 3 weeks after the first administration. At 5 to 10 days after each administration, blood is sampled from the eyeground venous plexus and the serum of each sample is tested for its ability to react with the antigen by enzyme immunoassay [Enzyme Immunoassay (ELISA): published by Igaku-Shoin Ltd., Japan, 1976], etc. A mouse or rat whose serum shows a sufficient antibody titer against the antigen is provided for use as a source of antibody-producing cells. For fusion between spleen cells and myeloma cells, spleens are excised from the immunized mice or rats at 3 to 4 days after the final administration of the antigen substance to collect their spleen cells. The spleens are minced in a serum-free basal medium (hereinafter referred to as washing medium) and centrifuged to collect the cells, followed by treatment with Tris-ammonium chloride buffer (pH 7.65) for 2 to 3 minutes to remove erythrocytes. The resulting cells are washed with the washing medium and then provided for use as spleen cells for fusion.

(3) Preparation of Myeloma Cells

As myeloma cells, established cells derived from mice are used. Examples include 8-azaguanine-resistant mouse (BALB/c) myeloma cell lines P3-X63Ag8-U1 (P3-U1) [Current Topics in Microbiology and Immunology-1, European J. Immunology, 6, 511-519 (1976)], SP2/O—Ag14 (SP-2) [Nature 276, 269-270 (1978)], P3-X63-Ag8653 (653) [J Immunology 123, 1548-1550 (1979)] and P3-X63-Ag8 (X63) [Nature 256, 495-497 (1975)], etc. These cell lines are subcultured in 8-azaguanine medium [RPMI-1640 medium containing glutamine (1.5 mM), 2-mercaptoethanol ($5 \times 10^{-5}$ M), gentamicin (10 μg/ml) and 10% fetal calf serum (FCS) (hereinafter referred to as normal medium), which is further supplemented with 8-azaguanine (15 μg/ml)], although they are transferred to and subcultured in the normal medium at 3 to 4 days prior to cell fusion to thereby ensure cell counts equal to or greater than $2 \times 10^7$ cells on the day of fusion.

(4) Cell Fusion

The antibody-producing cells immunized in (2) and the myeloma cells obtained in (3) are washed well with the washing medium or PBS (1.83 g of disodium phosphate, 0.21 g of monopotassium phosphate, 7.65 g of sodium chloride, 1 liter of distilled water, pH 7.2) and mixed together at a cell count ratio of antibody-producing cells to myeloma cells=5:1 to 10:1. After being collected, the cells are dissociated well and washed under stirring at 37° C. with a mixed solution containing 2 g of polyethylene glycol-1, 500 (PEG-1,500), 2 ml of the washing medium and 0.7 ml of dimethyl sulfoxide in a volume of 0.2 to 1 ml per $10^8$ antibody-producing cells, followed by several additions of the washing medium (1 to 2 ml) every 1 to 2 minutes to give a total volume of 50 ml. After being collected, the cells are gently dissociated and suspended in 100 ml of HAT medium [normal medium supplemented with hypoxanthine (10 M), thymidine ($1.5 \times 10^{-5}$ M) and aminopterin ($4 \times 10^{-7}$ M)]. This suspension is dispensed into 96-well culture plates in a volume of 100 μl/well and cultured in a 5% $CO_2$ incubator at 37° C. for 7 to 14 days. After culture, the culture supernatants are sampled and tested, for example, by using FACS (which is an abbreviation of fluorescence-activated cell sorting) or the like to select an antibody specifically reacting to the LAT1/CD98 protein. Then, cloning is repeated twice by limiting dilution techniques [using HT medium (HAT medium free from aminopterin) for the first cloning and the normal medium for the second cloning] to select a clone stably showing a strong antibody titer as an anti-LAT1/CD98 monoclonal antibody-producing hybridoma line.

Thus, in another related embodiment of the present invention, there is provided a method for preparation of a monoclonal antibody specifically binding to the extracellular region of LAT1/CD98, which comprises culturing such hybridoma cells and collecting an antibody specifically binding to LAT1/CD98 from the resulting cultured product.

4 Immunoconjugate of the Antibody of the Present Invention

In another embodiment, the present invention also provides an immunoconjugate formed between the antibody of the present invention or an antigen-binding fragment thereof and a compound with cell killing activity and/or antitumor activity or a radioisotope.

The antibody of the present invention is excellent in internalization activity into target tumor cells expressing LAT1/CD98. For this reason, its immunoconjugate formed with a compound with cell killing activity and/or antitumor activity allows this compound to directly and selectively act on the tumor cells.

5. Pharmaceutical Composition

In yet another embodiment, the present invention also provides a pharmaceutical composition for prevention or treatment or diagnosis of tumor, which contains the antibody of the present invention or an antigen-binding fragment thereof or an immunoconjugate therewith as an active ingredient. The pharmaceutical composition of the present invention further contains a pharmaceutically acceptable carrier.

As shown in the Example section described later, the antibody of the present invention or an antigen-binding fragment thereof specifically binds to the extracellular region of LAT1/CD98 in LAT1/CD98-expressing cells (e.g., tumor cells) to inhibit the activity of LAT1/CD98 or induce cytotoxic factors, whereby these cells can be led to cell death. Moreover, because of having internalization activity, its immunoconjugate formed with a compound with cell killing activity and/or antitumor activity allows this compound to directly and selectively act on tumor cells. Examples of such a compound include a cytotoxic drug, an antitumor agent or a radioisotope. Thus, the pharmaceutical composition of the present invention can be used for killing tumor cells that express LAT1/CD98 on their cell surface or for preventing or treating tumors characterized by such cells and diseases developed through a similar mechanism.

Furthermore, sensitivity and/or specificity of the therapeutic antibody of the present invention to cancer or tumor cells can be improved by the technique of T cell therapy which utilizes a chimeric antigen receptor (CAR) in the treatment of cancer or tumors (i.e., CAR-T cell therapy).

CAR-T cell therapy is a cellular immunotherapy which involves administration to a cancer patient genetically engineered T-cells that act on tumor cells and cause apoptosis of the tumor cells. The genetically engineered T cells are prepared by expressing on a T cell a CAR having variable regions of an antibody (VL and VH) combined with a CD3 chain (intracellular domain) using gene transfer technique. CAR is a general term for a chimeric protein in which a light chain (VL) and a heavy chain (VH) of a variable region of a monoclonal antibody specific for a tumor antigen are linked in series, which are then linked to a T-cell receptor (TCR) chain at the C-terminal side. More details of CAR-T cell therapy are described in Nakazawa (Shinshu Medical Journal, 61 (4): 197-203, 2013, 197-203) which is herein incorporated by reference in its entirety.

Examples of the above "tumors" include colorectal cancer, colon and rectal cancer, lung cancer, breast cancer, brain tumor, melanoma, renal cell carcinoma, bladder cancer, leukemia, lymphoma, T cell lymphoma, multiple myeloma, gastric cancer, pancreatic cancer, uterine cervical cancer, endometrial cancer, ovarian cancer, esophageal cancer, liver cancer, head and neck squamous cell carcinoma, skin cancer, urinary tract cancer, prostate cancer, choriocarcinoma, pharyngeal cancer, laryngeal cancer, tongue cancer, oral cancer, gallbladder cancer, thyroid cancer, mesothelioma, pleural tumor, arrhenoblastoma, endometrial hyperplasia, endometriosis, embryoma, fibrosarcoma, Kaposi's sarcoma, hemangioma, cavernous hemangioma, hemangioblastoma, retinoblastoma, astrocytoma, neurofibroma, oligodendroglioma, medulloblastoma, neuroblastoma, neuroglioma, rhabdomyosarcoma, glioblastoma, osteogenic sarcoma, leiomyosarcoma, thyroid sarcoma, and Wilms tumor, etc. More preferred examples include colorectal cancer, colon and rectal cancer, lung cancer, breast cancer, brain tumor, bladder cancer, lymphoma, gastric cancer, pancreatic cancer, liver cancer, and prostate cancer. When used as a pharmaceutical preparation, the antibody of the present invention or an antigen-binding fragment thereof may be formulated in accordance with conventionally used means. For example, the antibody or antigen-binding fragment thereof may be used parenterally in the form of injections such as sterile solutions or suspensions with water or any other pharmaceutically acceptable liquid. Alternatively, the antibody may be converted into IgA, conjugated with secretory component and then formulated into optionally sugar-coated tablets, capsules, elixirs, microcapsules or the like for oral use. For example, the antibody or antigen-binding fragment thereof may be mixed with physiologically acceptable known carriers, aromas, excipients, vehicles, antiseptics, stabilizers, binders and so on in a unit dose form required for generally accepted drug implementation. The amount of the active ingredient in these formulations makes a suitable dosage within the indicated range acquirable.

The phrase "pharmaceutically acceptable" is used herein to refer to those compounds, materials, compositions and/or dosage forms which are, within the scope of sound medical judgment, suitable for use in contact with the tissues of humans and animals without excessive toxicity, irritation, allergic response, or other problems or complications, and are commensurate with a reasonable benefit/risk ratio.

The route of administration of the pharmaceutical composition of the present invention for prevention or treatment of tumor is in accordance with well known methods, e.g., injection or infusion by intravenous, intraperitoneal, intracerebral, subcutaneous, intramuscular, intraocular, intraarterial, intracerebrospinal or intralesional route or by sustained release systems. Furthermore, the antibody or antigen-binding fragment thereof may also be administered through a catheter or the like as a means for direct administration to tumor sites.

Moreover, the pharmaceutical composition of the present invention for prevention or treatment of tumor may further comprise, e.g., a buffering agent (e.g., phosphate buffer, sodium acetate buffer), a soothing agent (e.g., benzalkonium chloride, procaine hydrochloride or the like), a stabilizer (e.g., human serum albumin, polyethylene glycol or the like), a preservative (e.g., benzyl alcohol, phenol or the like), an antioxidant and so on. The prepared injections are generally filled into appropriate ampules. The thus obtained formulations are safe and less toxic, and hence can be administered to mammals including humans. The dose of the antibody or antigen-binding fragment thereof or a salt thereof will vary depending on a subject to be administered, symptoms, the mode of administration, etc. For oral administration, the daily dose is usually about 0.1 to 100 mg, preferably about 1.0 to 50 mg, and more preferably about 1.0 to 20 mg, e.g., in patients with endometriosis or adenomyosis uteri (calculated as 60 kg). For parenteral administration, the dose will vary depending on a subject to be administered, symptoms, the mode of administration, etc. For example, in the form of injections, the daily dose, e.g., for 60 kg patients may usually be about 0.01 to 30 mg, preferably about 0.1 to 20 mg, and more preferably about 0.1 to 10 mg, given by intravenous injection.

6. Tumor Diagnostic Method of the Present Invention

In yet another embodiment, the present invention is also characterized by tumor detection with a diagnostic immunoconjugate formed between the antibody of the present invention or an antigen-binding fragment thereof described above and at least one diagnostic or detection agent. Preferably, such a diagnostic or detection agent is selected from the group consisting of a radionuclide, a contrast medium, a fluorescent agent, a chemiluminescent agent, a bioluminescent agent, a paramagnetic ion, an enzyme and a photoactive diagnostic agent. In one embodiment, the diagnostic immunoconjugate is reacted with a sample taken from a living organism (e.g., a tissue or blood sample) to detect signals, whereby tumor can be detected. Assays used for this purpose include, for example, ELISA, EI, RIA, fluorescent immunoassay, chemiluminescent immunoassay and so on. In yet another embodiment, the present invention can be used for PET imaging with a diagnostic immunoconjugate comprising a diagnostic radionuclide.

The present invention will now be described in more detail by way of the following examples, which are not intended to limit the scope of the present invention.

EXAMPLES

Example 1

(1) Immunization of Animals and Preparation of Antibody-Producing Cells

For preparation of anti-LAT1/CD98 monoclonal antibody, rats were immunized with a cell line highly expressing LAT1/CD98 (e.g., human colorectal cancer cell line HCT116) to collect antibody-producing cells from their spleens. For immunization, $3 \times 10^6$ cells of the cell line were administered as an antigen to the rats subcutaneously, intraperitoneally or intravenously. Administration of the antigen was repeated twice at 3 and 6 weeks after the first administration. For fusion between spleen cells and myeloma cells, spleens were excised from the immunized rats at 3 days after the final administration of the antigen to collect their spleen cells. The spleens were minced in a serum-free basal medium (hereinafter referred to as washing medium) and centrifuged to collect the cells, followed by treatment with Tris-ammonium chloride buffer (pH 7.65) for 2 to 3 minutes to remove erythrocytes. The resulting cells were washed with the washing medium and then used as spleen cells for fusion.

(2) Preparation of Hybridomas

The mouse or rat spleen cells obtained in Example 1(2) and mouse myeloma cell line X63 were mixed at a ratio of 4:1 and centrifuged at 1,200 rpm for 5 minutes to discard the supernatant. The precipitated cells were dissociated well and then supplemented under stirring at 37° C. with a mixed solution containing 2 g of polyethylene glycol-1500 (PEG-1500), 2 ml of DMEM medium and 0.7 ml of dimethyl sulfoxide in a volume of 0.2 to 1 ml per $10^8$ mouse spleen cells, followed by several additions of DMEM medium (1 to 2 ml) every 1 to 2 minutes and further addition of DMEM medium to give a total volume of 50 ml. After centrifugation at 900 rpm for 5 minutes to discard the supernatant, the cells were gently suspended in HAT medium (100 ml). This suspension was dispensed into 96-well culture plates in a volume of 100 µl/well and cultured in a 5% $CO_2$ incubator at 37° C. for 10 to 14 days.

(3) Antibody Screening

The hybridoma culture supernatants obtained in Example 1(3) were each reacted with another cell line (e.g., human lung cancer cell line NCI-H1944) highly expressing LAT1/CD98 and being distinct from the cell line used as an antigen, followed by FCM analysis to conduct primary screening as to whether or not an LAT1/CD98-specific antibody was produced.

The FCM reaction was conducted in 96-well plates. The cell line highly expressing LAT1/CD98 was adjusted with PBS to $2.5 \times 10^5$ to $3 \times 10^6$ cells/well and dispensed into tubes in 50 µl volumes. To this cell suspension, 50 µl culture supernatant of each hybridoma was added and reacted at 4° C. for 45 minutes. After washing three times by addition of 0.1% BSA-PBS (100 µL) and the subsequent centrifugation at 500 g for 3 minutes at 4° C., the cell pellets were each supplemented with 50 µL of 200-fold diluted PE-labeled anti-rat IgG (Jackson Immuno Research) and reacted under light-shielded conditions at 4° C. for 45 minutes. After washing three times by addition of 0.1% BSA-PBS (100 µL) and the subsequent centrifugation at 500 g for 3 minutes at 4° C., the cells were suspended in PBS (500 μL) and then transferred to FCM tubes. PI (100 μL) was added immediately before measurement to remove dead cells, followed by measurement with a FACS calibur (Becton Dickinson). Clones showing positive reaction were selected to establish four lines of anti-LAT1/CD98 antibody-producing hybridomas (LG9111, LG9112, LG9113 and LG9114).

(4) Purification of Monoclonal Antibodies

Pristine-treated nude male mice (KSN) at 8 weeks of age were administered intraperitoneally with each of the hybridoma lines obtained in Example 1(4) at $1 \times 10^7$ cells/animal After 10 to 15 days, the hybridomas became cancerous in ascites. Ascites was collected from each mouse showing ascites accumulation, centrifuged at 2000 rpm for 5 minutes at 4° C. and salted out with 50% saturated ammonium sulfate. The sediment was dissolved and centrifuged at 10000 g for 10 minutes at 4° C. After passing through a prefilter and a membrane filter (0.22 μm), the filtrate was purified with Protein G Sepharose (GE Healthcare Biosciences) and then dialyzed against PBS (for 3 hours or longer, repeated four times). The thus obtained four types of anti-LAT1/CD98 monoclonal antibodies were designated as LG9111 monoclonal antibody, LG9112 monoclonal antibody, LG9113 monoclonal antibody and LG9114 monoclonal antibody.

Example 2

Study on Binding Ability of Monoclonal Antibodies to Tumor Cell Lines

Using four types of human tumor cell lines, the anti-LAT1/CD98 monoclonal antibodies were measured for their binding ability by FCM analysis. The human tumor cell lines were each adjusted with PBS to $1 \times 10^5$ cells/well and dispensed into tubes in 50 μL volumes. To this cell suspension, 50 μL of each monoclonal antibody prepared at 40 μg/mL was added and reacted at 4° C. for 45 minutes. After washing three times by addition of 0.1% BSA-PBS (100 μL) and the subsequent centrifugation at 500 g for 3 minutes at 4° C., the cell pellets were each supplemented with 50 μL of 200-fold diluted PE-labeled anti-rat IgG (Jackson Immuno Research) and reacted under light-shielded conditions at 4° C. for 45 minutes. After washing three times by addition of 0.1% BSA-PBS (100 μL) and the subsequent centrifugation at 500 g for 3 minutes at 4° C., the cells were suspended in PBS (500 μL) and then transferred to FCM tubes. PI (100 μL) was added immediately before measurement to remove dead cells, followed by measurement with a FACS calibur (Becton Dickinson). As shown in FIG. 1, the obtained four types of monoclonal antibodies were found to show binding activity to various cancer cell lines, particularly high binding activity to colorectal cancer cell line HCT116. In addition, these monoclonal antibodies were found to have 10-fold or more higher binding activity than LGtra01-01 monoclonal antibody (i.e., the antibody disclosed in JP 2011-24537 A).

Example 3

Preparation of Human Chimeric Antibodies

Total RNA was separated from each of the established anti-LAT1/CD98 antibody-producing hybridoma lines and cDNA was synthesized with a SMARTer™ RACE cDNA Amplification Kit (Clontech). The resulting cDNA was subjected to polymerase chain reaction (PCR) to amplify cDNAs encoding heavy and light chain variable regions, which were then subcloned into cloning vectors. The nucleotide sequences of the resulting cDNAs were analyzed to determine the amino acid sequences (SEQ ID NOs: 31 to 38) of heavy and light chain variable regions of the respective antibodies and the amino acid sequences (SEQ ID NOs: 7 to 30) of their complementarity determining regions (CDRs) in a standard manner (described in www.bioinf.org.uk/abs/). CDR sequence-specific primers were synthesized and used to amplify CDRs from the extracted plasmid DNAs, and the resulting CDRs were integrated into a human chimeric antibody heavy chain expression vector or a human chimeric antibody light chain expression vector. The resulting plasmids were ligated together with ligase to prepare a plasmid for human chimeric antibody production. Using FreeStyle™ MAX Reagent (Invitrogen), the thus obtained plasmids for human chimeric antibody production were each transfected into FreeStyle 293F cells (Invitrogen), and the culture supernatants were collected after gyratory culture (FreeStyle™ 293 medium, 37° C., 8% $CO_2$, 135 rpm) for 96 hours. The culture supernatants were purified with Protein G Sepharose (GE Healthcare Biosciences) and then dialyzed against PBS (for 3 hours or longer, repeated four times) to obtain human chimeric LAT1/CD98 antibodies.

Example 4

Study on Antibody-Dependent Cellular Cytotoxicity Mediated by Human Chimeric Antibodies Blood was collected from a human subject into a heparinized blood collection tube (Terumo VP-H100K). The blood was diluted 2-fold with PBS, and the diluted heparinized blood (18 mL) was gently overlaid onto 12 mL of Lymphosepar I (IBL 23010). After centrifugation at 400 g for 30 minutes, the upper plasma layer was gently removed and a mononuclear cell fraction was isolated from the middle layer. The mononuclear cell fraction was diluted 2-fold with PBS and centrifuged at 200 g for 10 minutes to remove the supernatant. After washing twice by addition of PBS (10 mL) and the subsequent centrifugation at 200 g for 10 minutes, the cells were suspended in 5% FBS-RPMI1640 and used as an effector cell suspension. On the other hand, for use as target cells, human tumor cells were suspended at $2 \times 10^5$ cells/mL in 5% FBS-RPMI1640 and dispensed in 50 μL volumes into a U-bottomed 96-well plate at $1 \times 10^4$ cells/well. The human chimeric antibodies (50 μL each) were added and incubated at 4° C. for 15 minutes, followed by centrifugation to discard the supernatants. The effector cell suspension was added in 100 μL volumes (at the same time, a well containing the effector cells alone (Effector Spontaneous) and a well containing the target cells alone (Target Spontaneous) were prepared as controls) and incubated at 37° C. under 5% $CO_2$ for 4 hours (at the same time, a well where the target cells were supplemented with 10× Lysis buffer at 45 minutes before completion (Terget Max) was prepared as a control). After incubation, the cells were lightly shaken and centrifuged at 200 g for 5 minutes, and their supernatants (50 μL each) were transferred to a flat-bottomed 96-well plate. Cytotox96 Non-Radioactive cytotoxicity assay (Promega G1780) was used for reaction in accordance with the protocols attached to the kit, followed by measurement at 490 nm fluorescence wavelength with a plate reader (TECAN Infinite M200) to calculate the cytotoxic rate by the following equation. Cytotoxic rate (%)= (Experimental−Effector Spontaneous−Target Spontaneous)/

Figure 2:
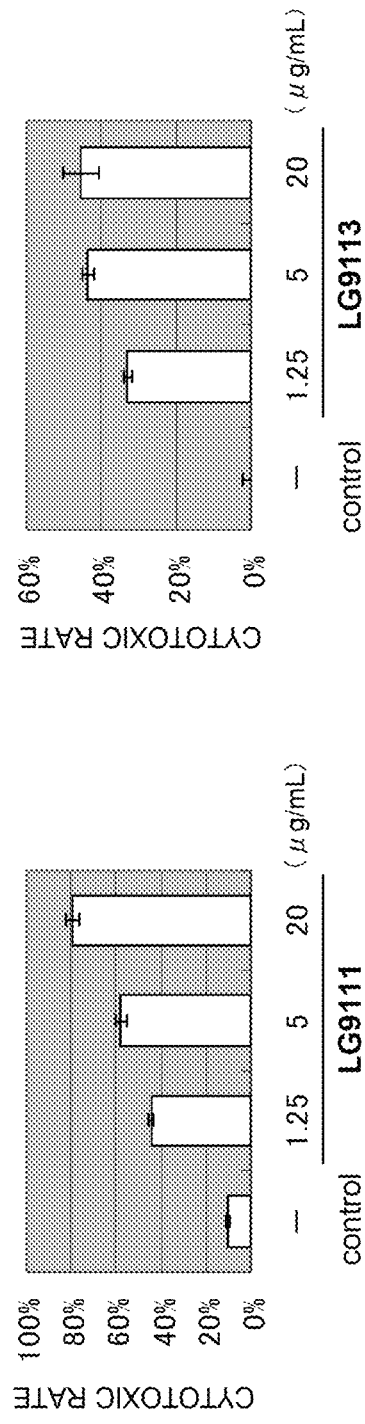
FIG. 2(A) shows the ADCC activity obtained with the use of human chimeric antibodies LG9111 and LG9113. Each panel shows the cytotoxic rates (%) obtained in the presence of human chimeric antibody added at 1.25 μg/mL, 5 μg/mL and 20 μg/mL and in the absence of the antibody, i.e., in the presence of effector cells and target cells alone as a control.
FIG. 2(B) shows the ADCC activity of human chimeric antibodies LG9111 and LG9113 on human colorectal cancer cell line (HCT116) and human lung cancer cell line (NCI-H1944).
Figure 2:
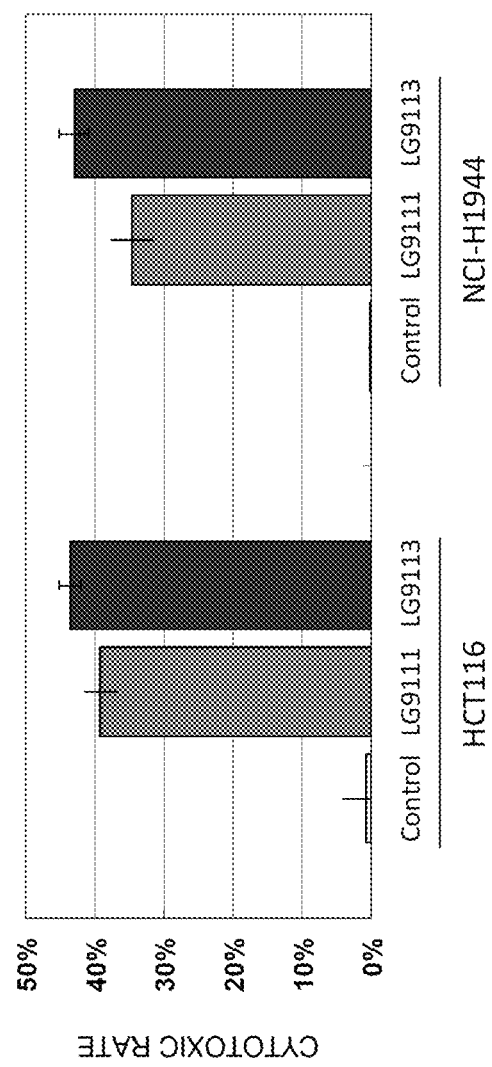

(Target Max−Target Spontaneous)×100. As shown in FIG. 2, in the LG9111 and LG9113 human chimeric antibodies, ADCC activity was detected in an antibody concentration-dependent manner, and these human chimeric antibodies were found to achieve a cytotoxic rate of 79% and 46%, respectively, against the human colorectal cancer cell line (HCT116) at an antibody concentration of 20 µg/mL. Moreover, they were also found to achieve a cytotoxic rate of 35% or more against the human lung cancer cell line (NCI-H1944).

Example 5

Study on Internalization Activity of Monoclonal Antibodies

Figure 3A:
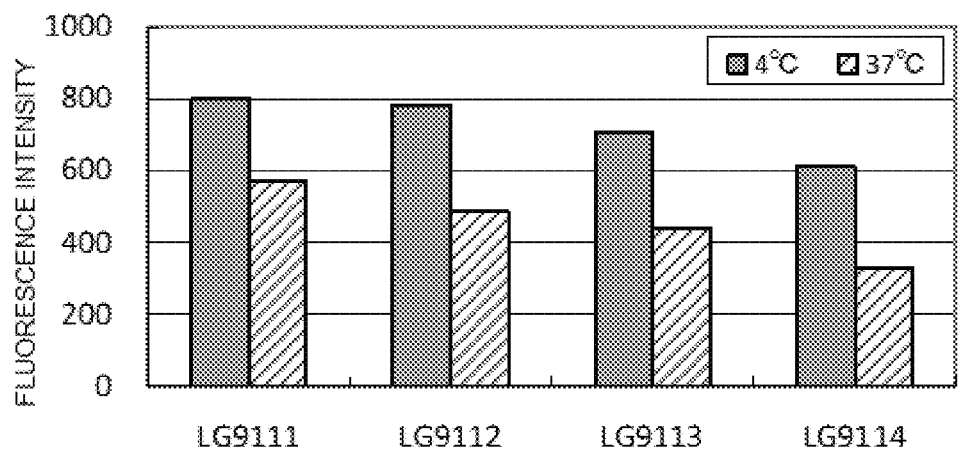
FIG. 3(A) shows the internalization activity of monoclonal antibodies LG9111, LG9112, LG9113 and LG9114.

Using a human tumor cell line, the anti-LAT1/CD98 monoclonal antibodies were measured for their internalization activity by FCM analysis. The human colorectal cancer cell line HCT116 was suspended in 0.1% BSA-PBS and dispensed in 50 µL volumes into a U-bottomed 96-well plate at $1 \times 10^5$ cells/well. To this cell suspension, 50 µL of each monoclonal antibody prepared at 20 µg/mL was added and reacted at 4° C. for 45 minutes. After washing three times by addition of 0.1% BSA-PBS (150 µL) and the subsequent centrifugation at 500 g for 3 minutes at 4° C., cell pellets bound with the monoclonal antibodies were obtained. To each cell pellet, 0.1% BSA-PBS (100 µL) was added and incubated for 1 hour at 37° C. (at which internalization is induced) or 4° C. (at which internalization is not induced). After washing three times by addition of 0.1% BSA-PBS (150 µL) and the subsequent centrifugation at 500 g for 3 minutes at 4° C., the cell pellets were each supplemented with 50 µL of 200-fold diluted PE-labeled anti-rat IgG (Jackson Immuno Research) and reacted under light-shielded conditions at 4° C. for 30 minutes. After washing three times by addition of 0.1% BSA-PBS (150 µL) and the subsequent centrifugation at 500 g for 3 minutes at 4° C., the cells were suspended in PBS (500 µL) and then transferred to FCM tubes. PI (100 µL) was added immediately before measurement to remove dead cells, followed by measurement with a FACS calibur (Becton Dickinson). As shown in FIG. 3(A), a reduction of fluorescence intensity induced by monoclonal antibody binding was observed upon incubation at 37° C. when compared to incubation at 4° C.

Figure 3B:
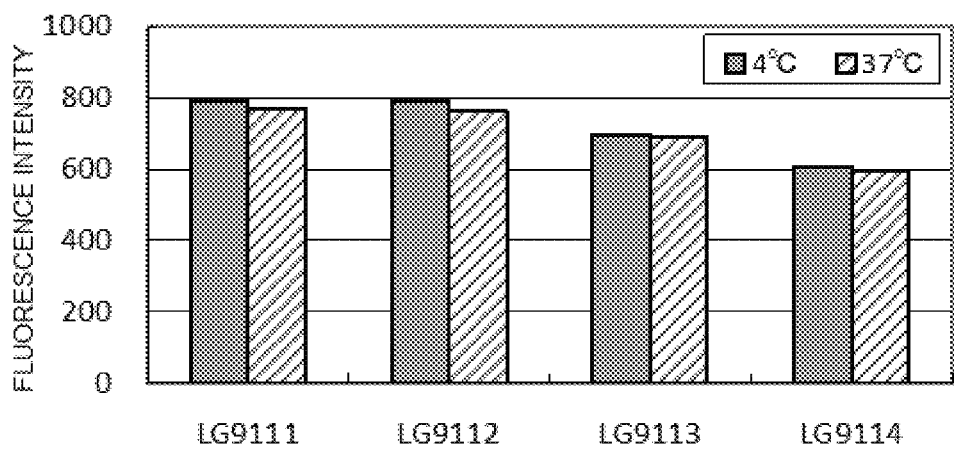
FIG. 3(B) indicates that the internalization activity shown in (A) is not false positive due to detachment of the monoclonal antibodies. Data is expressed as a value (ΔMFI) calculated by subtracting the control MFI upon reaction with rat IgG from the MFI upon reaction with each monoclonal antibody under conditions of 37° C. (at which internalization is induced) or 4° C. (at which internalization is not induced).

Moreover, to confirm that the reduction of fluorescence intensity is not caused when the monoclonal antibodies, once bound to the antigen, were detached from the antigen during incubation, the above cell pellets were reacted with the PE-labeled anti-rat IgG in the same manner, washed and then incubated for 1 hour at 37° C. (at which internalization is induced) or 4° C. (at which internalization is not induced). After washing, the same measurement was conducted with a FACS calibur. A shown in FIG. 3(B), there was no difference in fluorescence intensity between incubation at 4° C. and incubation at 37° C.

These results indicated that binding of the monoclonal antibodies to the antigen resulted in a reduction of the number of antigen-antibody complexes on the cell surface, i.e., caused internalization.

As demonstrated in Examples 2 to 4, the anti-LAT1/CD98 antibodies of the present invention have a significantly higher binding ability to the extracellular region of the LAT1/CD98 complex when compared to the previously reported anti-LAT1/CD98 antibody, and they are also excellent in cytotoxic activity against cells expressing the LAT1/CD98 complex.

INDUSTRIAL APPLICABILITY

The present invention is useful for induction of apoptosis in tumor cells highly expressing LAT1/CD98, or for pathological analysis, prevention, treatment or the like of tumors characterized by tumor cells highly expressing LAT1/CD98.

Sequence Listing Free Text

SEQ ID NO: 7: LG9111 light chain complementarity determining region 1 (CDRL1)
SEQ ID NO: 8: LG9111 light chain complementarity determining region 2 (CDRL2)
SEQ ID NO: 9: LG9111 light chain complementarity determining region 3 (CDRL3)
SEQ ID NO: 10: LG9111 heavy chain complementarity determining region 1 (CDRH1)
SEQ ID NO: 11: LG9111 heavy chain complementarity determining region 2 (CDRH2)
SEQ ID NO: 12: LG9111 heavy chain complementarity determining region 3 (CDRH3)
SEQ ID NO: 13: LG9112 light chain complementarity determining region 1 (CDRL1)
SEQ ID NO: 14: LG9112 light chain complementarity determining region 2 (CDRL2)
SEQ ID NO: 15: LG9112 light chain complementarity determining region 3 (CDRL3)
SEQ ID NO: 16: LG9112 heavy chain complementarity determining region 1 (CDRH1)
SEQ ID NO: 17: LG9112 heavy chain complementarity determining region 2 (CDRH2)
SEQ ID NO: 18: LG9112 heavy chain complementarity determining region 3 (CDRH3)
SEQ ID NO: 19: LG9113 light chain complementarity determining region 1 (CDRL1)
SEQ ID NO: 20: LG9113 light chain complementarity determining region 2 (CDRL2)
SEQ ID NO: 21: LG9113 light chain complementarity determining region 3 (CDRL3)
SEQ ID NO: 22: LG9113 heavy chain complementarity determining region 1 (CDRH1)
SEQ ID NO: 23: LG9113 heavy chain complementarity determining region 2 (CDRH2)
SEQ ID NO: 24: LG9113 heavy chain complementarity determining region 3 (CDRH3)
SEQ ID NO: 25: LG9114 light chain complementarity determining region 1 (CDRL1)
SEQ ID NO: 26: LG9114 light chain complementarity determining region 2 (CDRL2)
SEQ ID NO: 27: LG9114 light chain complementarity determining region 3 (CDRL3)
SEQ ID NO: 28: LG9114 heavy chain complementarity determining region 1 (CDRH1)
SEQ ID NO: 29: LG9114 heavy chain complementarity determining region 2 (CDRH2)
SEQ ID NO: 30: LG9114 heavy chain complementarity determining region 3 (CDRH3)
SEQ ID NO: 31: LG9111 light chain variable region
SEQ ID NO: 32: LG9111 heavy chain variable region
SEQ ID NO: 33: LG9112 light chain variable region
SEQ ID NO: 34: LG9112 heavy chain variable region
SEQ ID NO: 35: LG9113 light chain variable region
SEQ ID NO: 36: LG9113 heavy chain variable region
SEQ ID NO: 37: LG9114 light chain variable region
SEQ ID NO: 38: LG9114 heavy chain variable region

The invention claimed is:

1. An antibody or an antigen-binding fragment thereof, each specifically binding to the extracellular region of the LAT1/CD98 complex in LAT1/CD98-expressing cells, which is:

(1) an antibody or an antigen-binding fragment thereof, which comprises, as light chain complementarity determining region 1 (CDRL1), light chain complementarity determining region 2 (CDRL2) and light chain complementarity determining region 3 (CDRL3), the amino acid sequences of SEQ ID NO: 7, SEQ ID NO: 8 and SEQ ID NO: 9, respectively, and which comprises, as heavy chain complementarity determining region 1 (CDRH1), heavy chain complementarity determining region 2 (CDRH2) and heavy chain complementarity determining region 3 (CDRH3), the amino acid sequences of SEQ ID NO: 10, SEQ ID NO: 11 and SEQ ID NO: 12, respectively;

(2) an antibody or an antigen-binding fragment thereof, which comprises, as CDRL1, CDRL2 and CDRL3, the amino acid sequences of SEQ ID NO: 13, SEQ ID NO: 14 and SEQ ID NO: 15, respectively, and which comprises, as CDRH1, CDRH2 and CDRH3, the amino acid sequences of SEQ ID NO: 16, SEQ ID NO: 17 and SEQ ID NO: 18, respectively;

(3) an antibody or an antigen-binding fragment thereof, which comprises, as CDRL1, CDRL2 and CDRL3, the amino acid sequences of SEQ ID NO: 19, SEQ ID NO: 20 and SEQ ID NO: 21, respectively, and which comprises, as CDRH1, CDRH2 and CDRH3, the amino acid sequences of SEQ ID NO: 22, SEQ ID NO: 23 and SEQ ID NO: 24, respectively; or (4) an antibody or an antigen-binding fragment thereof, which comprises, as CDRL1, CDRL2 and CDRL3, the amino acid sequences of SEQ ID NO: 25, SEQ ID NO: 26 and SEQ ID NO: 27, respectively, and which comprises, as CDRH1, CDRH2 and CDRH3, the amino acid sequences of SEQ ID NO: 28, SEQ ID NO: 29 and SEQ ID NO: 30, respectively.

2. An antibody or an antigen-binding fragment thereof, each specifically binding to the extracellular region of the LAT1/CD98 complex in LAT1/CD98-expressing cells, which comprises:
(1) light chain complementarity determining region 1 (CDRL1) comprising the amino acid sequence X$_1$ASQX$_2$VGNNVA (SEQ ID NO: 1);
(2) light chain complementarity determining region 2 (CDRL2) comprising the amino acid sequence YASX$_3$RX$_4$T (SEQ ID NO: 2);
(3) light chain complementarity determining region 3 (CDRL3) comprising the amino acid sequence QRX$_5$YKSPYT (SEQ ID NO: 3);
(4) heavy chain complementarity determining region 1 (CDRH1) comprising the amino acid sequence GFSLPTSSVS (SEQ ID NO: 4);
(5) heavy chain complementarity determining region 2 (CDRH2) comprising the amino acid sequence VIWSNGNTDYSSX$_6$X$_7$KS (SEQ ID NO: 5); and
(6) heavy chain complementarity determining region 3 (CDRH3) comprising the amino acid sequence NFRNX$_8$PGVMDA (SEQ ID NO: 6) (provided that X$_1$ to X$_8$ are each any naturally occurring amino acid residue).

3. The antibody or antigen-binding fragment thereof according to claim 2, wherein
X$_1$ is R or K,
X$_2$ is N or T,
X$_3$ is S or N,
X$_4$ is H or N,
X$_5$ is V or I,
X$_6$ is A or R,
X$_7$ is I or F, and
X$_8$ is D or N (SEQ ID NOS 39-43).

4. The antibody or antigen-binding fragment thereof according to claim 2, wherein

```
                                  (SEQ ID NOS 7-9 and 11-12)
(1) X₁ is R, X₂ is N, X₃ is N, X₄ is N, X₅ is I, X₆ is A, X₇ is I, and X₈ is D, (SEQ ID NOS 13-15 and 17-18)
(2) X₁ is K, X₂ is N, X₃ is S, X₄ is H, X₅ is V, X₆ is R, X₇ is F, and X₈ is D, (SEQ ID NOS 19-21 and 23-24)
(3) X₁ is K, X₂ is T, X₃ is S, X₄ is H, X₅ is V, X₆ is R, X₇ is F, and X₈ is D,
or (SEQ ID NOS 25-27 and 29-30)
(4) X₁ is K, X₂ is N, X₃ is S, X₄ IS H, X₅ is V, X₆ is R, X₇ is I, and X₈ is N.
```

5. The antibody or antigen-binding fragment thereof according to claim 1, which contains:
(1) a light chain variable region (VL) comprising an amino acid sequence sharing an identity of 90% or more with the amino acid sequence of SEQ ID NO: 31, and
a heavy chain variable region (VH) comprising an amino acid sequence sharing an identity of 90% or more with the amino acid sequence of SEQ ID NO: 32;
(2) a light chain variable region (VL) comprising an amino acid sequence sharing an identity of 90% or more with the amino acid sequence of SEQ ID NO: 33, and
a heavy chain variable region (VH) comprising an amino acid sequence sharing an identity of 90% or more with the amino acid sequence of SEQ ID NO: 34;
(3) a light chain variable region (VL) comprising an amino acid sequence sharing an identity of 90% or more with the amino acid sequence of SEQ ID NO: 35, and
a heavy chain variable region (VH) comprising an amino acid sequence sharing an identity of 90% or more with the amino acid sequence of SEQ ID NO: 36; or
(4) a light chain variable region (VL) comprising an amino acid sequence sharing an identity of 90% or more with the amino acid sequence of SEQ ID NO: 37, and
a heavy chain variable region (VH) comprising an amino acid sequence sharing an identity of 90% or more with the amino acid sequence of SEQ ID NO: 38.

6. An antibody or antigen-binding fragment thereof, each specifically binding to the extracellular region of the LAT1/CD98-expressing cells, which contains:
(1) a light chain variable region (VL) comprising the amino acid sequence of SEQ ID NO: 31, and
a heavy chain variable region (VH) comprising the amino acid sequence of SEQ ID NO: 32;
(2) a light chain variable region (VL) comprising the amino acid sequence of SEQ ID NO: 33, and
a heavy chain variable region (VH) comprising the amino acid sequence of SEQ ID NO: 34;
(3) a light chain variable region (VL) comprising the amino acid sequence of SEQ ID NO: 35, and
a heavy chain variable region (VH) comprising the amino acid sequence of SEQ ID NO: 36; or
(4) a light chain variable region (VL) comprising the amino acid sequence of SEQ ID NO: 37, and
a heavy chain variable region (VH) comprising the amino acid sequence of SEQ ID NO: 38.

7. The antibody or antigen-binding fragment thereof according to claim 1, which has cytotoxic activity and/or internalization activity on LAT1/CD98-expressing cells.

8. The antibody or antigen-binding fragment thereof according to claim 1, whose subclass is IgG.

9. The antibody or antigen-binding fragment thereof according to claim 8, wherein the IgG is IgG$_{2a}$ or IgG$_1$.

10. The antibody or antigen-binding fragment thereof according to claim 1, wherein the antigen-binding fragment is any of Fab, Fab', F(ab')$_2$, scFv, dsFv, ds-scFv, dimers, minibodies, diabodies and multimers thereof, or a bispecific antibody fragment.

11. The antibody or antigen-binding fragment thereof according to claim 1, which is a monoclonal antibody.

12. The antibody or antigen-binding fragment thereof according to claim 1, which is a rat, mouse, primate or human antibody.

13. The antibody or antigen-binding fragment thereof according to claim 1, which is a chimeric antibody or a humanized antibody.

14. An immunoconjugate, which comprises the antibody or antigen-binding fragment thereof according to claim 1 and at least one cytotoxic drug, antitumor agent or radioisotope.

15. An isolated nucleic acid molecule, which encodes the antibody or antigen-binding fragment thereof according to claim 1.

16. An expression vector, which comprises the nucleic acid molecule according to claim 15.

17. A hybridoma cell or a transgenic cell, each producing the antibody according to claim 1, which comprises a nucleic acid molecule which encodes the antibody or antigen-binging fragment thereof according to claim 1, or is transformed with the nucleic acid molecule.

18. A method for preparation of a monoclonal antibody specifically binding to the extracellular region of the LAT1/CD98 complex, which comprises culturing the cell according to claim 17 and collecting an antibody specifically binding to the LAT1/CD98 complex from the resulting cultured product.

19. A method for preparation of a monoclonal antibody specifically binding to the extracellular region of LAT1/CD98, which comprises isolating nucleic acid molecules encoding a VH and VL of an anti-LAT1/CD98 monoclonal antibody from the cell according to claim 17, constructing an expression vector comprising the gene, introducing the expression vector into a host to cause expression of the monoclonal antibody, and collecting the monoclonal antibody specifically binding to the extracellular region of LAT1/CD98 from the resulting host, the culture supernatant of the host or the secretory product of the host.

20. The method for preparation according to claim 19, wherein the host is *E. coli*, a yeast cell, an insect cell, a mammalian cell, or a plant cell.

21. A composition containing the antibody or antigen-binding fragment thereof according to claim 1, which is used for induction of apoptosis by being applied to LAT1/CD98-expressing cells.

22. A composition containing the antibody or antigen-binding fragment thereof according to claim 1, which is used for detection of LAT1/CD98-expressing cells.

23. A method for in vitro immunological detection of tumor, which comprises the step of contacting the composition according to claim 22 with cancer cells.

24. A method for in vivo imaging of tumor, which comprises the steps of administering the composition according to claim 22 to a subject and obtaining a detection image by near-infrared optical imaging, PET, MRI or ultrasonic imaging.

25. A pharmaceutical preparation for detecting LAT1/CD98 complex in tumor cells, which contains the antibody or antigen-binding fragment thereof according to claim 1.

26. A chimeric antigen receptor (CAR) comprising the heavy chain variable region (VH) and the light chain variable region (VL) as defined in (1), (2), (3) or (4) of claim 5.

27. A genetically modified T cell having the CAR according to claim 26 being expressed on its surface (CAR-T cell).

28. The pharmaceutical preparation according to claim 25, wherein the tumor is at least one selected from the group consisting of colorectal cancer, colon and rectal cancer, lung cancer, breast cancer, brain tumor, melanoma, renal cell carcinoma, bladder cancer, leukemia, lymphoma, T cell lymphoma, multiple myeloma, gastric cancer, pancreatic cancer, uterine cervical cancer, endometrial cancer, ovarian cancer, esophageal cancer, liver cancer, head and neck squamous cell carcinoma, skin cancer, urinary tract cancer, prostate cancer, choriocarcinoma, pharyngeal cancer, laryngeal cancer, tongue cancer, oral cancer, gallbladder cancer, thyroid cancer, mesothelioma, pleural tumor, arrhenoblastoma, endometrial hyperplasia, endometriosis, embryoma, fibrosarcoma, Kaposi's sarcoma, hemangioma, cavernous hemangioma, hemangioblastoma, retinoblastoma, astrocytoma, neurofibroma, oligodendroglioma, medulloblastoma, neuroblastoma, neuroglioma, rhabdomyosarcoma, glioblastoma, osteogenic sarcoma, leiomyosarcoma, thyroid sarcoma, and Wilms tumor.

29. A chimeric antigen receptor (CAR) comprising the heavy chain variable region (VH) and the light chain variable region (VL) as defined in (1), (2), (3) or (4) of claim 6.

30. A composition comprising the immunoconjugate according to claim 14, which is used for induction of apoptosis by being applied to LAT1/CD98-expressing cells.

31. A composition comprising the immunoconjugate according to claim 14, which is configured for detecting LAT1/CD98-expressing cells.

* * * * *

SEQUENCE LISTING

<160> NUMBER OF SEQ ID NOS: 43

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      Mus musculus x Rattus norvegicus peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (5)..(5)
<223> OTHER INFORMATION: Any amino acid

<400> SEQUENCE: 1

Xaa Ala Ser Gln Xaa Val Gly Asn Asn Val Ala
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      Mus musculus x Rattus norvegicus peptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid

<400> SEQUENCE: 2

Tyr Ala Ser Xaa Arg Xaa Thr
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      Mus musculus x Rattus norvegicus peptide
<220> FEATURE:
<221> NAME/KEY: MOD_RES
<222> LOCATION: (3)..(3)
<223> OTHER INFORMATION: Any amino acid

<400> SEQUENCE: 3

Gln Arg Xaa Tyr Lys Ser Pro Tyr Thr
1               5

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      Mus musculus x Rattus norvegicus peptide

<400> SEQUENCE: 4

Gly Phe Ser Leu Pro Thr Ser Ser Val Ser
1               5                   10

```
<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence: Synthetic
      Mus musculus x Rattus norvegicus peptide
<220> FEATURE:
<221> NAME/KEY: MOD_RES
<222> LOCATION: (13)..(14)
<223> OTHER INFORMATION: Any amino acid

<400> SEQUENCE: 5

Val Ile Trp Ser Asn Gly Asn Thr Asp Tyr Ser Ser Xaa Xaa Lys Ser
1               5                   10                  15

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      Mus musculus x Rattus norvegicus peptide
<220> FEATURE:
<221> NAME/KEY: MOD_RES
<222> LOCATION: (5)..(5)
<223> OTHER INFORMATION: Any amino acid

<400> SEQUENCE: 6

Asn Phe Arg Asn Xaa Pro Gly Val Met Asp Ala
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      Mus musculus x Rattus norvegicus peptide

<400> SEQUENCE: 7

Arg Ala Ser Gln Asn Val Gly Asn Asn Val Ala
1               5                   10

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      Mus musculus x Rattus norvegicus peptide

<400> SEQUENCE: 8

Tyr Ala Ser Asn Arg Asn Thr
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      Mus musculus x Rattus norvegicus peptide

<400> SEQUENCE: 9

Gln Arg Ile Tyr Lys Ser Pro Tyr Thr
1               5

<210> SEQ ID NO 10
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      Mus musculus x Rattus norvegicus peptide

<400> SEQUENCE: 10

Gly Phe Ser Leu Pro Thr Ser Ser Val Ser
1               5                   10

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
      Mus musculus x Rattus norvegicus peptide

<400> SEQUENCE: 11

Val Ile Trp Ser Asn Gly Asn Thr Asp Tyr Ser Ser Ala Ile Lys Ser
1               5                   10                  15

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      Mus musculus x Rattus norvegicus peptide

<400> SEQUENCE: 12

Asn Phe Arg Asn Asp Pro Gly Val Met Asp Ala
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      Mus musculus x Rattus norvegicus peptide

<400> SEQUENCE: 13

Lys Ala Ser Gln Asn Val Gly Asn Asn Val Ala
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      Mus musculus x Rattus norvegicus peptide

<400> SEQUENCE: 14

Tyr Ala Ser Ser Arg His Thr
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      Mus musculus x Rattus norvegicus peptide

<400> SEQUENCE: 15
```

Gln Arg Val Tyr Lys Ser Pro Tyr Thr
1               5

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      Mus musculus x Rattus norvegicus peptide

<400> SEQUENCE: 16

Gly Phe Ser Leu Pro Thr Ser Ser Val Ser
1               5                   10

<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence: Synthetic
      Mus musculus x Rattus norvegicus peptide

<400> SEQUENCE: 17

Val Ile Trp Ser Asn Gly Asn Thr Asp Tyr Ser Ser Arg Phe Lys Ser
1               5                   10                  15

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      Mus musculus x Rattus norvegicus peptide

<400> SEQUENCE: 18

Asn Phe Arg Asn Asp Pro Gly Val Met Asp Ala
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      Mus musculus x Rattus norvegicus peptide

<400> SEQUENCE: 19

Lys Ala Ser Gln Thr Val Gly Asn Asn Val Ala
1               5                   10

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      Mus musculus x Rattus norvegicus peptide

<400> SEQUENCE: 20

Tyr Ala Ser Ser Arg His Thr
1               5

<210> SEQ ID NO 21
<211> LENGTH: 9
<212> TYPE: PRT
<213> ORGANISM: Artificial Sequence
<220> FEATURE:

<223> OTHER INFORMATION: Description of Artificial Sequence: Synthetic
      Mus musculus x Rattus norvegicus peptide

<400> SEQUENCE: 21

Gln Arg Val Tyr Lys Ser Pro Tyr Thr
1               5

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      Mus musculus x Rattus norvegicus peptide

<400> SEQUENCE: 22

Gly Phe Ser Leu Pro Thr Ser Ser Val Ser
1               5                   10

<210> SEQ ID NO 23
<211> LENGTH: 16
<212> TYPE: PRT
<213> ORGANISM: Artificial Sequence
<220> FEATURE:
<223> OTHER INFORMATION: Description of Artificial Sequence: Synthetic
      Mus musculus x Rattus norvegicus peptide

<400> SEQUENCE: 23

Val Ile Trp Ser Asn Gly Asn Thr Asp Tyr Ser Ser Arg Phe Lys Ser
1               5                   10                  15

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic
      Mus musculus x Rattus norvegicus peptide

<400> SEQUENCE: 24

Asn Phe Arg Asn Asp Pro Gly Val Met Asp Ala
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence: Synthetic
      Mus musculus x Rattus norvegicus peptide

<400> SEQUENCE: 25

Lys Ala Ser Gln Asn Val Gly Asn Asn Val Ala
1               5                   10

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      Mus musculus x Rattus norvegicus peptide

<400> SEQUENCE: 26

Tyr Ala Ser Ser Arg His Thr
1               5

```
<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      Mus musculus x Rattus norvegicus peptide

<400> SEQUENCE: 27

Gln Arg Val Tyr Lys Ser Pro Tyr Thr
1               5

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      Mus musculus x Rattus norvegicus peptide

<400> SEQUENCE: 28

Gly Phe Ser Leu Pro Thr Ser Ser Val Ser
1               5                   10

<210> SEQ ID NO 29
<211> LENGTH: 16
<212> TYPE: PRT
<213> ORGANISM: Artificial Sequence
<220> FEATURE:
<223> OTHER INFORMATION: Description of Artificial Sequence: Synthetic
      Mus musculus x Rattus norvegicus peptide

<400> SEQUENCE: 29

Val Ile Trp Ser Asn Gly Asn Thr Asp Tyr Ser Ser Arg Ile Lys Ser
1               5                   10                  15

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence: Synthetic
      Mus musculus x Rattus norvegicus peptide

<400> SEQUENCE: 30

Asn Phe Arg Asn Asn Pro Gly Val Met Asp Ala
1               5                   10

<210> SEQ ID NO 31
<211> LENGTH: 128
<212> TYPE: PRT
<213> ORGANISM: Artificial Sequence
<220> FEATURE:
<223> OTHER INFORMATION: Description of Artificial Sequence: Synthetic
      Mus musculus x Rattus norvegicus polypeptide

<400> SEQUENCE: 31

Met Glu Ser Gln Thr Gln Val Val Ile Phe Val Leu Leu Trp Leu Ser
1               5                   10                  15

Gly Ala Asn Gly Asn Ile Val Met Thr Gln Ser Pro Arg Ser Met Ser
            20                  25                  30

Leu Ser Gly Gly Asp Arg Val Thr Met Asn Cys Arg Ala Ser Gln Asn
        35                  40                  45

Val Gly Asn Asn Val Ala Trp Tyr Gln Gln Arg Pro Gly Gln Ser Pro
    50                  55                  60

Lys Leu Leu Ile Ser Tyr Ala Ser Asn Arg Asn Thr Gly Val Pro Gly
```

```
                65                  70                  75                  80
Arg Phe Thr Gly Ser Gly Ser Gly Thr Asp Phe Thr Leu Thr Ile Ser
                    85                  90                  95
Ser Val Gln Ala Glu Asp Ala Ala Phe Tyr Tyr Cys Gln Arg Ile Tyr
                100                 105                 110
Lys Ser Pro Tyr Thr Phe Gly Gly Gly Thr Lys Leu Glu Leu Lys Arg
            115                 120                 125
```

<210> SEQ ID NO 32
<211> LENGTH: 138
<212> TYPE: PRT
<213> ORGANISM: Artificial Sequence
<220> FEATURE:
<223> OTHER INFORMATION: Description of Artificial Sequence: Synthetic
      Mus musculus x Rattus norvegicus polypeptide

<400> SEQUENCE: 32

```
Met Ala Val Leu Val Leu Leu Cys Leu Leu Ile Phe Pro Ser Cys
1               5                   10                  15
Val Leu Ser Gln Leu Gln Leu Lys Glu Ser Gly Pro Gly Leu Val Gln
                20                  25                  30
Pro Ser Gln Thr Leu Ser Leu Thr Cys Thr Val Ser Gly Phe Ser Leu
            35                  40                  45
Pro Thr Ser Ser Val Ser Trp Ile Arg Gln Pro Pro Gly Lys Gly Leu
        50                  55                  60
Glu Trp Met Gly Val Ile Trp Ser Asn Gly Asn Thr Asp Tyr Ser Ser
65                  70                  75                  80
Ala Ile Lys Ser Arg Leu Ser Ile Ser Arg Asp Thr Ser Lys Ser Gln
                85                  90                  95
Val Phe Leu Lys Met Asn Ser Leu Gln Thr Glu Asp Thr Ala Arg Tyr
                100                 105                 110
Phe Cys Ala Arg Asn Phe Arg Asn Asp Pro Gly Val Met Asp Ala Trp
            115                 120                 125
Gly Gln Gly Ala Ser Val Thr Val Ser Ser
        130                 135
```

<210> SEQ ID NO 33
<211> LENGTH: 128
<212> TYPE: PRT
<213> ORGANISM: Artificial Sequence
<220> FEATURE:
<223> OTHER INFORMATION: Description of Artificial Sequence: Synthetic
      Mus musculus x Rattus norvegicus polypeptide

<400> SEQUENCE: 33

```
Met Glu Ser Gln Thr Gln Val Val Ile Phe Val Leu Leu Trp Leu Ser
1               5                   10                  15
Gly Ala Asn Gly Asn Ile Val Met Thr Gln Ser Pro Lys Ser Met Ser
                20                  25                  30
Ile Ser Val Gly Asp Arg Val Thr Met Asn Cys Lys Ala Ser Gln Asn
            35                  40                  45
Val Gly Asn Asn Val Ala Trp Tyr Gln Gln Lys Pro Gly Leu Ser Pro
        50                  55                  60
Lys Leu Leu Ile Ser Tyr Ala Ser Ser Arg His Thr Gly Val Pro Asp
65                  70                  75                  80
Arg Phe Thr Gly Arg Gly Ser Gly Ala Asp Phe Thr Leu Thr Ile Asn
                85                  90                  95
Gly Val Gln Ala Glu Asp Ala Ala Phe Tyr Tyr Cys Gln Arg Val Tyr
```

```
              100                 105                 110

Lys Ser Pro Tyr Thr Phe Gly Gly Gly Thr Lys Leu Glu Leu Lys Arg
        115                 120                 125

<210> SEQ ID NO 34
<211> LENGTH: 138
<212> TYPE: PRT
<213> ORGANISM: Artificial Sequence
<220> FEATURE:
<223> OTHER INFORMATION: Description of Artificial Sequence: Synthetic
      Mus musculus x Rattus norvegicus polypeptide

<400> SEQUENCE: 34

Met Ala Val Leu Val Leu Leu Leu Cys Leu Leu Ile Phe Pro Asn Cys
1               5                   10                  15

Val Leu Ser Gln Met Gln Leu Lys Glu Ser Gly Pro Gly Leu Val Gln
            20                  25                  30

Pro Ser Gln Thr Leu Ser Leu Thr Cys Ala Val Ser Gly Phe Ser Leu
        35                  40                  45

Pro Thr Ser Ser Val Ser Trp Ile Arg Gln Ser Pro Gly Lys Gly Leu
    50                  55                  60

Glu Trp Met Gly Val Ile Trp Ser Asn Gly Asn Thr Asp Tyr Ser Ser
65                  70                  75                  80

Arg Phe Lys Ser Arg Leu Ser Ile Ser Arg Asp Thr Ala Lys Ser Gln
                85                  90                  95

Val Phe Leu Lys Met Asn Ser Leu Gln Ala Glu Asp Thr Ala Met Tyr
            100                 105                 110

Phe Cys Ala Arg Asn Phe Arg Asn Asp Pro Gly Val Met Asp Ala Trp
        115                 120                 125

Gly Gln Gly Ala Ser Val Thr Val Ser Ser
    130                 135

<210> SEQ ID NO 35
<211> LENGTH: 128
<212> TYPE: PRT
<213> ORGANISM: Artificial Sequence
<220> FEATURE:
<223> OTHER INFORMATION: Description of Artificial Sequence: Synthetic
      Mus musculus x Rattus norvegicus polypeptide

<400> SEQUENCE: 35

Met Glu Ser Gln Thr Gln Val Val Ile Phe Val Leu Leu Trp Leu Ser
1               5                   10                  15

Gly Ala Asn Gly Asn Ile Val Met Thr Gln Ser Pro Lys Ser Met Ser
            20                  25                  30

Ile Ser Val Gly Asp Arg Val Thr Met Asn Cys Lys Ala Ser Gln Thr
        35                  40                  45

Val Gly Asn Asn Val Ala Trp Tyr Gln Gln Lys Pro Gly Leu Ser Pro
    50                  55                  60

Lys Leu Leu Ile Ser Tyr Ala Ser Ser Arg His Thr Gly Val Pro Asp
65                  70                  75                  80

Arg Phe Thr Gly Arg Gly Ser Gly Ala Asp Phe Thr Leu Thr Ile Asn
                85                  90                  95

Gly Val Gln Ala Glu Asp Ala Ala Phe Tyr Tyr Cys Gln Arg Val Tyr
            100                 105                 110

Lys Ser Pro Tyr Thr Phe Gly Gly Gly Thr Lys Leu Glu Leu Lys Arg
        115                 120                 125
```

<210> SEQ ID NO 36
<211> LENGTH: 138
<212> TYPE: PRT
<213> ORGANISM: Artificial Sequence
<220> FEATURE:
<223> OTHER INFORMATION: Description of Artificial Sequence: Synthetic
      Mus musculus x Rattus norvegicus polypeptide

<400> SEQUENCE: 36

Met Ala Val Leu Val Leu Leu Leu Cys Leu Leu Ile Phe Pro Asn Cys
1               5                   10                  15

Val Leu Ser Gln Met Gln Leu Lys Glu Ser Gly Pro Gly Leu Val Gln
                20                  25                  30

Pro Ser Gln Thr Leu Ser Leu Thr Cys Ala Val Ser Gly Phe Ser Leu
            35                  40                  45

Pro Thr Ser Ser Val Ser Trp Ile Arg Gln Ser Pro Gly Lys Gly Leu
        50                  55                  60

Glu Trp Met Gly Val Ile Trp Ser Asn Gly Asn Thr Asp Tyr Ser Ser
65                  70                  75                  80

Arg Phe Lys Ser Arg Leu Ser Ile Ser Arg Asp Thr Ala Lys Ser Gln
                85                  90                  95

Val Phe Leu Lys Met Asn Ser Leu Gln Thr Glu Asp Thr Ala Met Tyr
                100                 105                 110

Phe Cys Ala Arg Asn Phe Arg Asn Asp Pro Gly Val Met Asp Ala Trp
            115                 120                 125

Gly Gln Gly Ala Ser Val Thr Val Ser Ser
        130                 135

<210> SEQ ID NO 37
<211> LENGTH: 128
<212> TYPE: PRT
<213> ORGANISM: Artificial Sequence
<220> FEATURE:
<223> OTHER INFORMATION: Description of Artificial Sequence: Synthetic
      Mus musculus x Rattus norvegicus polypeptide

<400> SEQUENCE: 37

Met Glu Ser Gln Thr Gln Val Val Ile Phe Val Leu Leu Trp Leu Ser
1               5                   10                  15

Gly Ala Asn Gly Asn Ile Val Met Thr Gln Ser Pro Lys Ser Met Ser
                20                  25                  30

Ile Ser Val Gly Asp Arg Val Thr Met Asn Cys Lys Ala Ser Gln Asn
            35                  40                  45

Val Gly Asn Asn Val Ala Trp Tyr Gln Gln Lys Pro Gly Leu Ser Pro
        50                  55                  60

Lys Leu Leu Ile Tyr Tyr Ala Ser Ser Arg His Thr Gly Val Pro Asp
65                  70                  75                  80

Arg Phe Thr Gly Ser Gly Ser Gly Ala Asp Phe Thr Leu Thr Ile Asn
                85                  90                  95

Ser Val Gln Ala Glu Asp Ala Ala Phe Tyr Tyr Cys Gln Arg Val Tyr
                100                 105                 110

Lys Ser Pro Tyr Thr Phe Gly Gly Gly Thr Lys Leu Glu Leu Lys Arg
            115                 120                 125

<210> SEQ ID NO 38
<211> LENGTH: 138
<212> TYPE: PRT
<213> ORGANISM: Artificial Sequence
<220> FEATURE:
<223> OTHER INFORMATION: Description of Artificial Sequence: Synthetic Mus musculus x Rattus norvegicus polypeptide

<400> SEQUENCE: 38

```
Met Ala Val Leu Val Leu Leu Leu Cys Leu Leu Ile Phe Pro Ser Cys
1               5                   10                  15
Val Leu Ser Gln Met Gln Leu Lys Glu Ser Gly Pro Gly Leu Val Gln
            20                  25                  30
Pro Ser Gln Thr Leu Ser Leu Thr Cys Ala Val Ser Gly Phe Ser Leu
        35                  40                  45
Pro Thr Ser Ser Val Ser Trp Ile Arg Gln Ser Pro Gly Lys Gly Leu
    50                  55                  60
Glu Trp Met Gly Val Ile Trp Ser Asn Gly Asn Thr Asp Tyr Ser Ser
65                  70                  75                  80
Arg Ile Lys Ser Arg Leu Ser Ile Ser Arg Asp Thr Ser Lys Ser Gln
                85                  90                  95
Val Phe Leu Lys Met Asn Ser Leu Gln Thr Glu Asp Thr Ala Met Tyr
            100                 105                 110
Phe Cys Ala Arg Asn Phe Arg Asn Asn Pro Gly Val Met Asp Ala Trp
        115                 120                 125
Gly Gln Gly Ala Ser Val Thr Val Ser Ser
    130                 135
```

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
      Mus musculus x Rattus norvegicus peptide
<220> FEATURE:
<221> NAME/KEY: MOD_RES
<222> LOCATION: (1)..(1)
<223> OTHER INFORMATION: Arg or Lys
<220> FEATURE:
<221> NAME/KEY: MOD_RES
<222> LOCATION: (5)..(5)
<223> OTHER INFORMATION: Asn or Thr

<400> SEQUENCE: 39

```
Xaa Ala Ser Gln Xaa Val Gly Asn Asn Val Ala
1               5                   10
```

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      Mus musculus x Rattus norvegicus peptide
<220> FEATURE:
<221> NAME/KEY: MOD_RES
<222> LOCATION: (4)..(4)
<223> OTHER INFORMATION: Ser or Asn
<220> FEATURE:
<221> NAME/KEY: MOD_RES
<222> LOCATION: (6)..(6)
<223> OTHER INFORMATION: His or Asn

<400> SEQUENCE: 40

```
Tyr Ala Ser Xaa Arg Xaa Thr
1               5
```

<210> SEQ ID NO 41
<211> LENGTH: 9
<212> TYPE: PRT

```
<213> ORGANISM: Artificial Sequence
<220> FEATURE:
<223> OTHER INFORMATION: Description of Artificial Sequence: Synthetic
      Mus musculus x Rattus norvegicus peptide
<220> FEATURE:
<221> NAME/KEY: MOD_RES
<222> LOCATION: (3)..(3)
<223> OTHER INFORMATION: Val or Ile

<400> SEQUENCE: 41

Gln Arg Xaa Tyr Lys Ser Pro Tyr Thr
1               5

<210> SEQ ID NO 42
<211> LENGTH: 16
<212> TYPE: PRT
<213> ORGANISM: Artificial Sequence
<220> FEATURE:
<223> OTHER INFORMATION: Description of Artificial Sequence: Synthetic
      Mus musculus x Rattus norvegicus peptide
<220> FEATURE:
<221> NAME/KEY: MOD_RES
<222> LOCATION: (13)..(13)
<223> OTHER INFORMATION: Ala or Arg
<220> FEATURE:
<221> NAME/KEY: MOD_RES
<222> LOCATION: (14)..(14)
<223> OTHER INFORMATION: Ile or Phe

<400> SEQUENCE: 42

Val Ile Trp Ser Asn Gly Asn Thr Asp Tyr Ser Ser Xaa Xaa Lys Ser
1               5                   10                  15

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: Synthetic
      Mus musculus x Rattus norvegicus peptide
<220> FEATURE:
<221> NAME/KEY: MOD_RES
<222> LOCATION: (5)..(5)
<223> OTHER INFORMATION: Asp or Asn

<400> SEQUENCE: 43

Asn Phe Arg Asn Xaa Pro Gly Val Met Asp Ala
1               5                   10
```